(12) United States Patent
Tam et al.

(10) Patent No.: US 8,097,624 B2
(45) Date of Patent: Jan. 17, 2012

(54) CYCLOALKYL DERIVATIVES OF 3-HYDROXY-4-PYRIDINONES

(75) Inventors: Tim Fat Tam, Woodbridge (CA);
Michael Spino, Pickering (CA);
Wanren Li, Etobicoke (CA); Yingsheng Wang, Toronto (CA); Yanqing Zhao, Toronto (CA); Birenkumar Hasmukhbhai Shah, North York (CA)

(73) Assignee: Apotex Inc., Toronto (CA)

( * ) Notice: Subject to any disclaimer, the term of this patent is extended or adjusted under 35 U.S.C. 154(b) by 922 days.

(21) Appl. No.: 12/149,853

(22) Filed: May 9, 2008

(65) Prior Publication Data
US 2009/0170850 A1    Jul. 2, 2009

Related U.S. Application Data

(62) Division of application No. 10/580,011, filed on May 19, 2006, now Pat. No. 7,410,985.

(51) Int. Cl.
*A61K 31/5377*    (2006.01)
*A61K 31/44*    (2006.01)
*A61K 31/497*    (2006.01)
*C07D 213/78*    (2006.01)
*C07D 401/06*    (2006.01)
*C07D 413/06*    (2006.01)

(52) U.S. Cl. ................ 514/235.5; 514/253.11; 514/348; 544/131; 544/365; 546/298

(58) Field of Classification Search ......................... None
See application file for complete search history.

(56) References Cited

U.S. PATENT DOCUMENTS

| 5,480,894 | A | 1/1996 | Hider et al. |
| 5,688,815 | A | 11/1997 | Zbinden |
| RE35,948 | E | 11/1998 | Hider et al. |
| 6,335,353 | B1 | 1/2002 | Hider et al. |
| 6,426,418 | B1 | 7/2002 | Tam et al. |
| 6,472,532 | B1 | 10/2002 | Tam et al. |
| 6,476,229 | B1 | 11/2002 | Tam et al. |
| 6,488,273 | B2 | 12/2002 | Sawdon et al. |

FOREIGN PATENT DOCUMENTS

| CA | 2287907 | 12/1998 |
| CA | 2379370 | 9/2003 |

OTHER PUBLICATIONS

Tam, Tim F. et al; Iron-Chelating Research: Past, Present and Future, Current Medicinal Chemistry, Jun. 2003, vol. 10, No. 12, pp. 983-985.
Singh, S. et al.; Urinary Metabolic Profiles in Human and Rat of 1 ,2,Dimethyl- and1,2-Diethyl-Substituted . . . , Drug Metabolism Disposition, 1992, vol. 20 No. 2, pp. 256-261.
Voest et al.; Iron-Chelating Agents in Non-Iron Overload Conditions, Annals of Internal Medicine 1994, vol. 120, No. 6, pp. 490-499.
Van Asbeck B.S. et al.; Anti-HIV effect of iron chelators: different mechanisms involved, Journal of Clinical Virology Feb. 2001; vol. 20 No. 3, pp. 141-147.
Rakba, et al., Iron Mobilisation and Cellular Protection by a New Synthetic Chelator O-Trensox, Biochemical Pharmacology, 1998, 55(11), pp. 1797-1806.
International Search Report; PCT/CA2004/001986; Jun. 16, 2005.
Bartfay et al.; Cardiac function and cytotoxic aldehyde production in a murine model of chronic iron-overload, Cardiovascular Research, 1999, 43(4), pp. 892-900.
Bergeron et al.; A Comparison of the Iron-Clearing Properties of 1,2-Dimethyl-3-Hydroxypyrid-4-One . . . , blood, 1992, vol. 79, No. 7, pp. 1882-1890.
Crumbliss, A.L., Iron Chelation in Biology (http://www.medicine.uiowa.edu/FRRB/VirtualSchool/Crumbliss-Fe.pdf).
Dhungana, et al., Fe(III) Coordination Properties of a New Saccharide-Based Exocyclic Trihydroxamate Analogue . . . , Inorganic Chemisty, Jan. 13, 2003, 42(1), pp. 42-50.
Hendrickson et al, The Consequences of Chemical Bonding; Classes of Molecules, Organic Chemisty, Third Edition, 1970, McGraw Hill, p. 72.
Hershko, et al., The iron-loaded gerbil model revisited: Effects of Deferoxamine and deferiprone treatment, J. Lab. Clin, Med., 2002, vol. 139, No. 1, pp. 50-58.
King, R.E., Tablets, Capsules and Pills, Remington's Pharmaceutical Sciences, 15th Edition, 1975, Mack Publishing Company, Easton, PA, ch. 89, pp. 1576-1607.

(Continued)

*Primary Examiner* — Kamal Saeed

(57) ABSTRACT

The present invention provides an cycloalkyl derivative of 3-hydroxy-4-pyridinone which is useful for the chelation of metal ions such as iron. Its preparation and use is described. In particular, the invention concerns the removal of iron in chemical and biological systems including chelating agents having the formula I

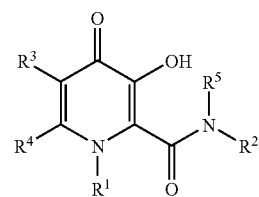

wherein $R^1$ is X with the proviso that $R^2$ is Y; or $R^1$ is T with the proviso that $R^2$ is W; or $R^1$ is X with the proviso that $R^2R^5N$ when taken together form a heterocyclic ring selected from piperidinyl, morpholinyl, pyrrolidinyl or piperazinyl, wherein the group piperidinyl, morpholinyl, pyrrolidinyl or piperazinyl is either unsubstituted or substituted with one to three $C_1$ to $C_6$ alkyl groups. X is $C_3$-$C_6$ cycloalkyl; Y is selected from the group consisting of $C_1$ to $C_6$ cycloalkyl; $C_1$ to $C_6$ alkyl, and $C_1$ to $C_6$ alkyl monosubstituted with a $C_3$-$C_6$ cycloalkyl; T is $C_1$ to $C_6$ alkyl; W is $C_3$-$C_6$ cycloalkyl; $R^3$ is selected from the group consisting of hydrogen and $C_1$ to $C_6$ alkyl; $R^4$ is selected from the group consisting of hydrogen and $C_1$ to $C_6$ alkyl; $R^5$ is selected from the group consisting of hydrogen and $C_1$ to $C_6$ alkyl; and its pharmaceutically acceptable salt thereof. Pharmaceutical compositions of such compounds are useful in the removal of excess body iron from patients with iron overload diseases.

6 Claims, 9 Drawing Sheets

OTHER PUBLICATIONS

Kontoghiorghes, G.J. Orally active a-Ketohydroxypyridine Iron Chelators: Studies in Mice, Molecular Pharmacology, 1986, 30(6), pp. 670-673.

Pernarowski, M., Solutions, Emulsions, and Suspensions, Remington's Pharmaceutical Sciences, 15th Edition, 1975, Mack Publishing Company, Easton, PA, ch. 83, pp. 1436-1460.

Pierre, J.L. and Fontecave, M. Iron and activated oxygen species in biology: The basic chemistry, BioMetals, 1999, 12, pp. 195-199.

Hider, R. C. and Zhou, Tao; The Design of Orally Acrtive Iron Chelators, Ann. N.Y. Academy of Sciences. 1054:141-154 (2005).

Tam, T.F. et al; Tris(1-cyclopropyl-6-methyl-2-(N-methylaminocarbonyl)-4-oxo-1,4-dihydropyridin-4-olato) iron(III) dimethylformamide sesquisolvate dihydrate; Acta Cyst. (2005); E61, m 2601-2603.

Figure 2:
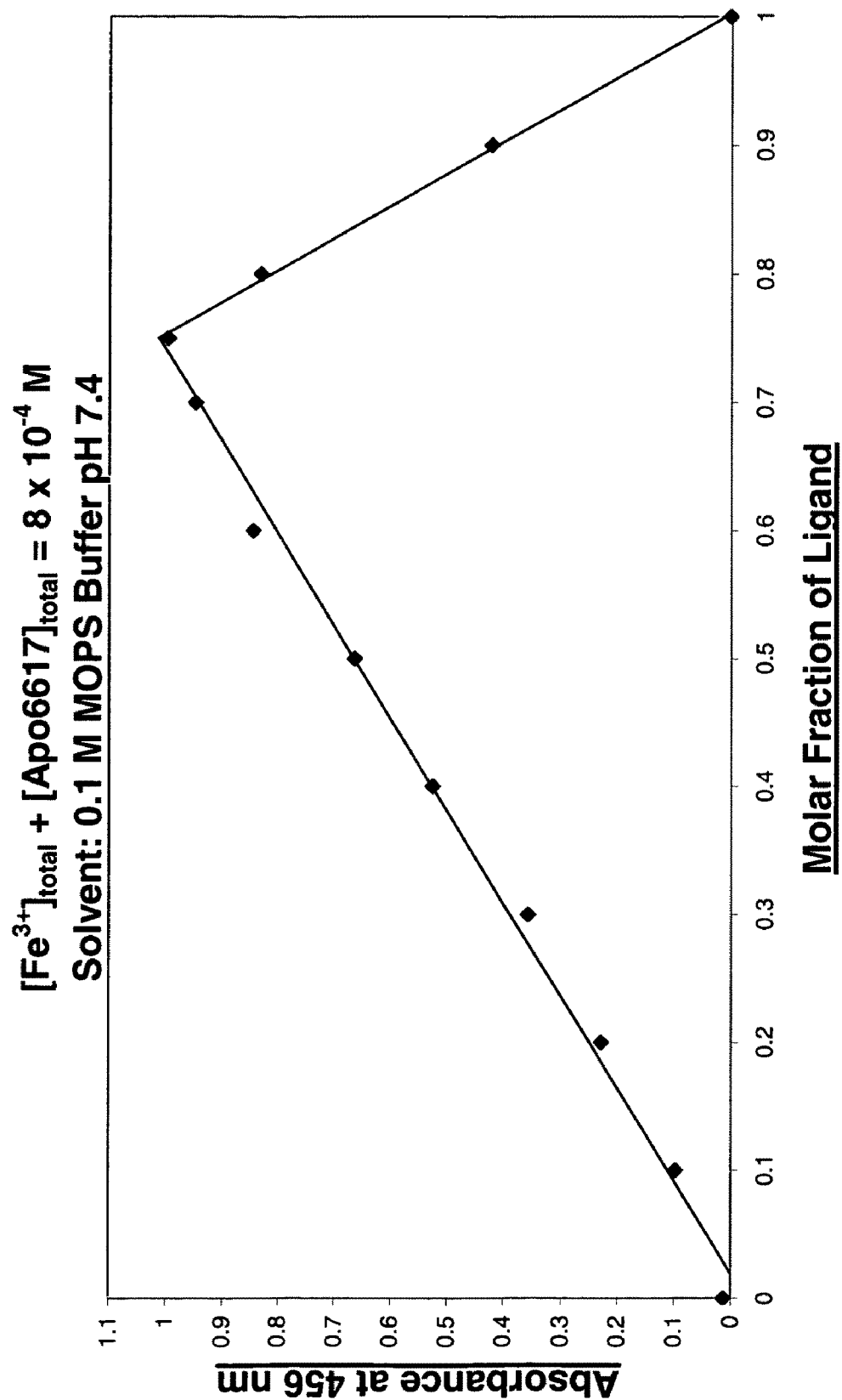

Figure 2: Job's Plot for Apo6617

Figure 3:
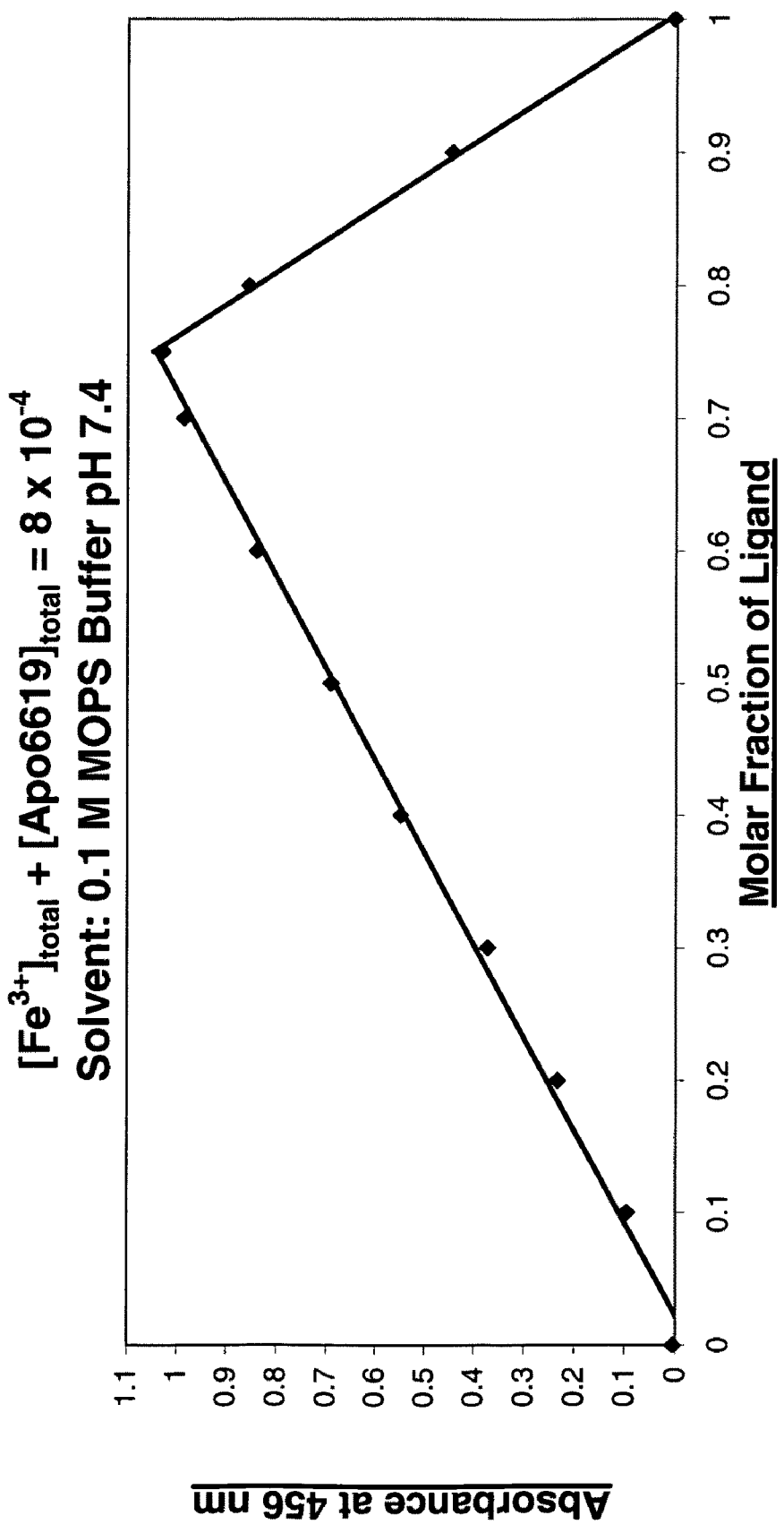

Figure 3: Job's Plot for Apo6619

Effectiveness of Apo6619 and Apo6617 in Promoting Urinary Iron Excretion

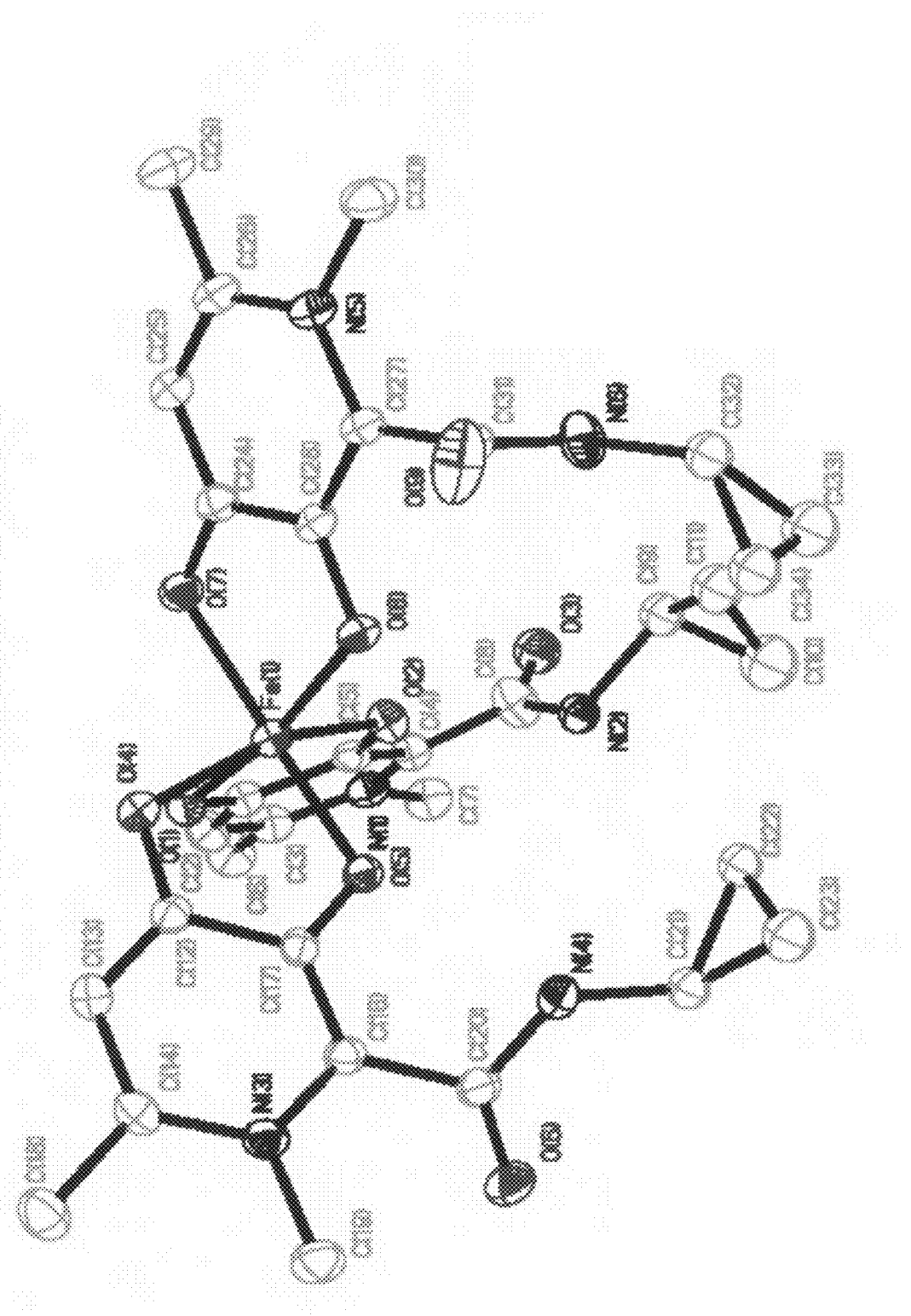

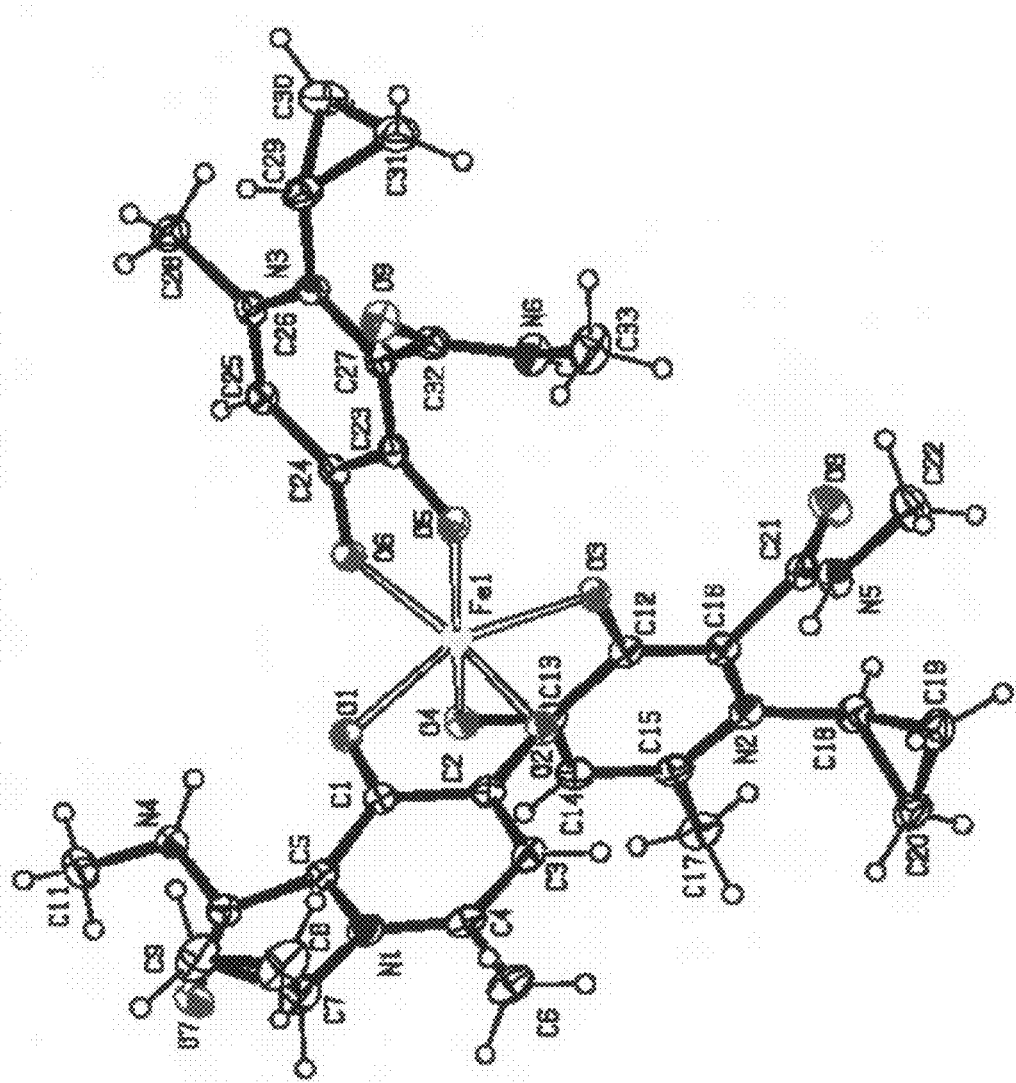

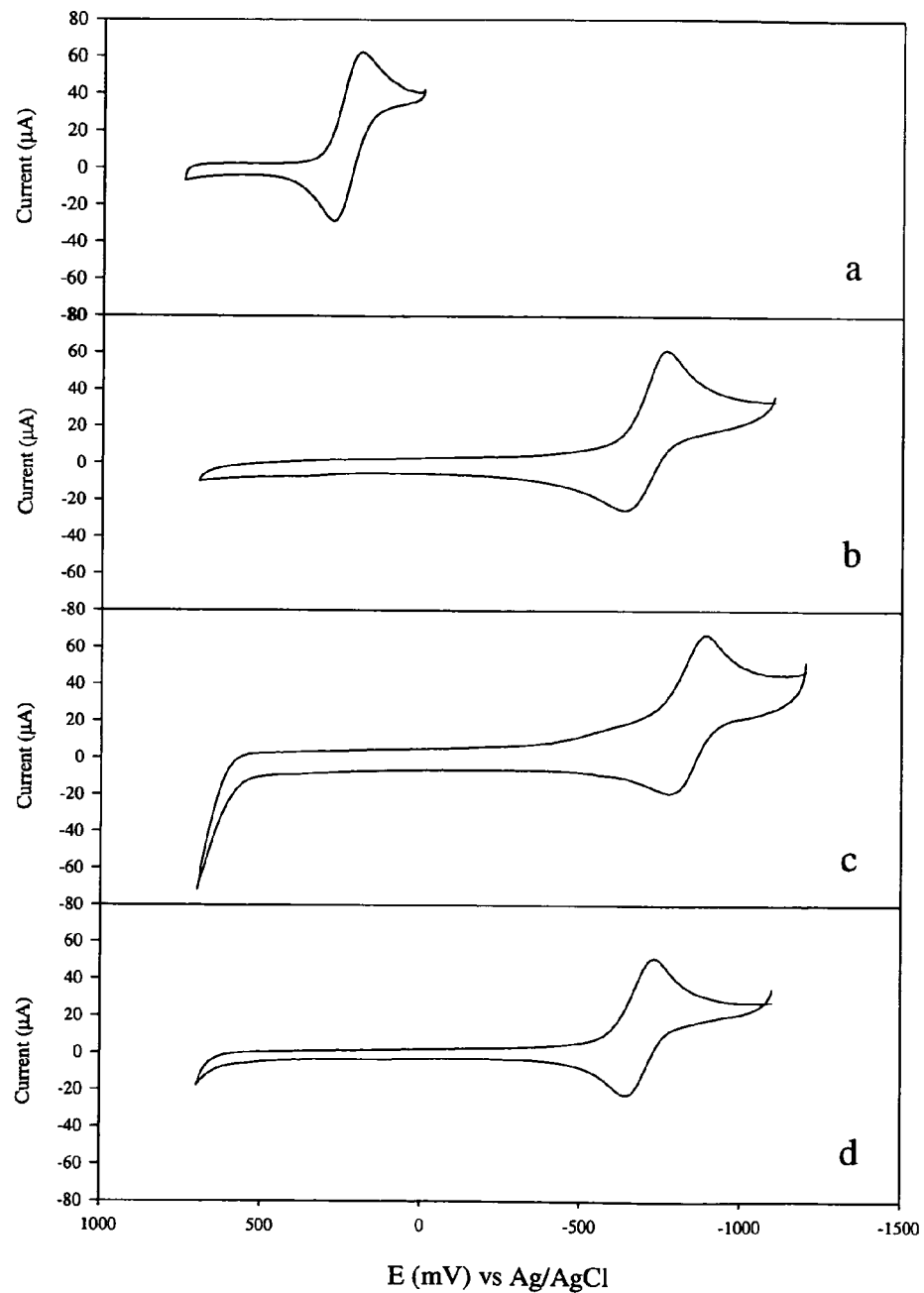
Figure 9: Cyclic voltammogram of a. $K_3Fe(CN)_6$; b. Fe(DFO); c. Fe(deferiprone); d. $Fe(Apo6619)_3$ at pH 7.4 $K_3Fe(CN)_6$ is used as a standard to validate the results

CYCLOALKYL DERIVATIVES OF 3-HYDROXY-4-PYRIDINONES

REFERENCE TO RELATED APPLICATION

This application is a divisional of U.S. patent application Ser. No. 10/580,011, filed on May 19, 2006 now U.S. Pat. No. 7,410,985.

FIELD OF THE INVENTION

The invention relates to novel 3-hydroxy-4-pyridinone derivatives and their use in chelating ferric (III) ions. More particularly, the invention relates to cycloalkyl derivatives of 3-hydroxy-4-pyridinone.

BACKGROUND

3-Hydroxy-4-pyridinones are bidentate ligands that chelate to the Fe(III) ion in the ratio of 3:1 and are useful in the removal of excess body iron in humans. Iron overload may be due to excess dietary consumption of iron, inherited genetic conditions such as haemochromatosis and regular blood transfusion. Such transfusions are used to treat medical conditions such as thalassaemia, sickle cell anaemia, idiopathic haemochromatosis and aplastic anaemia. Increased iron absorption from transfusion leads to iron overload. Upon saturation of ferritin and transferrin in the body, iron deposit in many tissues such as the myocardium, liver and endocrine organs resulting in toxic effects.

The scope of iron chelator research and the proposed utility of chelators have been reviewed (Current Medicinal Chemistry, 2003, 10, 983-985, Tim F. Tam, et al). Iron chelators may be useful to prevent hydroxy radical formation, treatment of cancer, malaria, post-ischaemic reperfusion, and neurodegenerative diseases. Iron chelators such as Desferal™ (desferrioxamine mesylate) and Ferriprox™ (deferiprone) are used to remove excess body iron in thalassemia major patients because the human body has no effective means to excrete the iron accumulated from blood transfusion. Desferrioxamine is administered daily by subcutaneous infusion over a period of 8 to 12 hours. At present, deferiprone (1,2-dimethyl-3-hydroxy-4-pyridinone) is the only orally drug available. It undergoes extensive metabolism in the liver and more than 85% of the administered dose is recovered in the urine as the non-chelating O-glucuronide (Drug Metab. Dispo. 1992, 20(2), 256-261, S. Singh, et al.). A relatively high oral dose of 75 mg/kg (3.5 to 4 gm per day) is required for the treatment of iron overload conditions. Therefore, there is a need to identify a new orally active hydroxypyridinone with improved pharmacological properties than deferiprone.

Voest et. al. (Annals of Internal Medicine 1994, 120, 490-499) reviewed the clinical experience of iron chelators in non-iron overloaded conditions. Iron chelators were used to produce antioxidant effects, antiproliferative effects, antiprotozal effects and for aluminum chelation, and may be used be for a variety of disease state such as the treatment of rheumatoid arthritis, the protection against anthracycline cardiac poisoning, for limiting mycocardial ischemia-reperfusion injury, as antitumour agents, and for the treatment of malaria. In addition, van Asbeck B. S. et. al. (J Clin Virol. 2001 February; 20(3):141-7) reported that iron chelators have anti-HIV activities. Therefore the utitlies of iron chelators are not only restricted to the treatment of iron-overloaded conditions.

The members of the 3-hydroxy-4-pyridinones class are known for their ability to chelate iron. Prior art includes RE 35,948, U.S. Pat. No. 6,448,273, U.S. Pat. No. 6,335,353 and U.S. Pat. No. 5,480,894. In U.S. Pat. No. 6,335,353, the ester prodrug derivatives of 3-hydroxy-4-pyridinones are used to facilitate efficient iron extraction from the liver, however none of the designed compounds has reached evaluation in humans.

In other approaches, selected new compounds were designed to block the phase II metabolism of O-glucuronidation at the C3 oxygen of the deferiprone skeleton. U.S. Pat. No. 5,688,815 reported 1-alkyl-3-hydroxy-4-pyridinones with a C2 methyl group substituted with a phenyl or heteroyl ring and a hydroxy group, and the N1 substituent being a lower alkyl. U.S. Pat. No. 6,335,353 described 1-alkyl-3-hydroxy-4-pyridinone with a C2 alkylcarbamoyl, arylcarbamoyl, or an aralkylcarbamoyl group and the N1-substituent is an aliphatic hydrocarbon group. The use of C2-methylcarbamoyl functionality in compound such as CP502 (1,6-Dimethyl-3-hydroxy-4(1H)-pyridinone-2-carboxy-(N-methyl)-amide hydrochloride; U.S. Pat. No. 6,335,353) effectively blocked the O-glucuronidation at the C3 oxygen. Other analogues in U.S. Pat. No. 6,335,353 include CP506 (1,6-Dimethyl-3-hydroxy-4(1H)-pyridinone-2-carboxy-(N-isopropyl)-amide hydrochloride), the C2-isopropylcarbamoyl analogue and CP508 (1,6-Dimethyl-3-hydroxy-4(1H)-pyridinone-2-carboxy-(N,N-dimethyl)-amide hydrochloride), the dimethylcarbamoyl analogue. CP502, CP506 and CP508 are prior art and have not been evaluated in humans.

SUMMARY OF THE INVENTION

A first aspect of the present invention provides a 3-hydroxypyridin-4-one compound of formula I inclusive of a pharmaceutically acceptable salt of the compound of formula I,

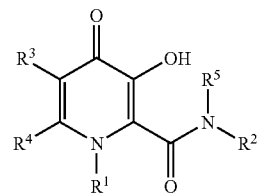

wherein:
$R^1$ is X with the proviso that $R^2$ is Y; or
$R^1$ is T with the proviso that $R^2$ is W; or
$R^1$ is X with the proviso that $R^2R^5N$ when taken together, form a heterocyclic ring selected from piperidinyl, morpholinyl, pyrrolidinyl or piperazinyl, wherein the group piperidinyl, morpholinyl, pyrrolidinyl or piperazinyl is either unsubstituted or substituted with one to three $C_1$-$C_6$ alkyl groups;
X is $C_3$-$C_6$ cycloalkyl;
Y is selected from the group consisting of $C_3$-$C_6$ cycloalkyl, $C_1$ to $C_6$ alkyl and $C_1$ to $C_6$ alkyl monosubstituted with a $C_3$-$C_6$ cycloalkyl;
T is $C_1$ to $C_6$ alkyl;
W is $C_3$-$C_6$ cycloalkyl;
$R^3$ is selected from the group consisting of hydrogen and $C_1$-$C_6$ alkyl;
$R^4$ is selected from the group consisting of hydrogen and $C_1$-$C_6$ alkyl; and
$R^5$ is selected from the group consisting of hydrogen and $C_1$-$C_6$ alkyl.

A second aspect of the present invention provides use of a compound of formula I in the treatment of iron overload related disease.

A third aspect of the invention provides a pharmaceutical composition comprising a compound of formula I.

One preferred class of compounds of this invention is the compound of formula I wherein $R^1$ is X with the proviso that $R^2$ is Y, X is $C_3$-$C_6$ cycloalkyl, Y is $C_1$ to $C_6$ alkyl, $R^3$ is hydrogen, $R^4$ is $C_1$-$C_6$ alkyl and $R^5$ is hydrogen.

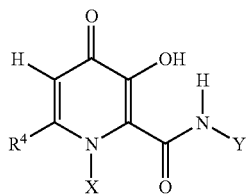

A still more preferred compound under this subset is a compound of formula I wherein $R^4$ is methyl, X is cyclopropyl and Y is methyl and the compound is 1-cyclopropyl-3-hydroxy-6-methyl-4-oxo-1,4-dihydro-pyridine-2-carboxylic acid methylamide.

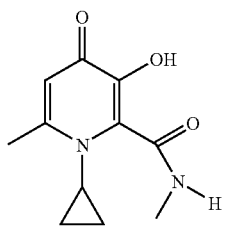

A second preferred class of compounds of this invention is a compound of formula I wherein $R^1$ is X with the proviso that $R^2$ is Y, X is $C_3$-$C_6$ cycloalkyl, Y is $C_3$-$C_6$ cycloalkyl, $R^3$ is hydrogen, $R^4$ is $C_1$-$C_6$ alkyl and $R^5$ is hydrogen.

A preferred compound within this subset is a compound wherein $R^4$ is methyl, X=Y=cyclopropyl and the compound is 1-cyclopropyl-3-hydroxy-6-methyl-4-oxo-1,4-dihydro-pyridine-2-carboxylic acid cyclopropylamide.

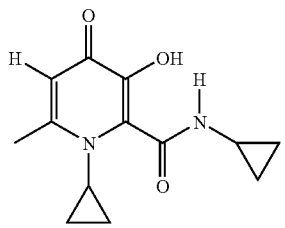

A third preferred class of compounds of formula I is a compound wherein $R^1$ is T with the proviso that $R^2$ is W, T is $C_1$ to $C_6$ alkyl, W is $C_3$-$C_6$ cycloalkyl, $R^3$ is hydrogen, $R^4$ is $C_1$-$C_6$ alkyl and $R^5$ is hydrogen.

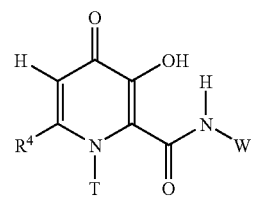

A more preferred compound under this subset is a compound wherein $R^4$ is methyl, T is methyl and W is cyclopropyl, the compound is 3-hydroxy-1,6-dimethyl-4-oxo-1,4-dihydro-pyridine-2-carboxylic acid cyclopropylamide.

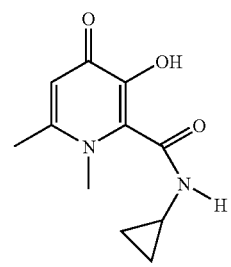

A fourth preferred class of compounds of this invention is a compound of formula I wherein $R^1$ is X with the proviso that $R^2$ is Y, X is $C_3$-$C_6$ cycloalkyl, Y is $C_1$ to $C_6$ alkyl, $R^3$ is hydrogen, $R^4$ is $C_1$-$C_6$ alkyl, and $R^5$ is methyl.

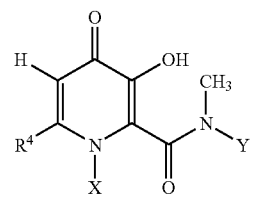

A still more preferred compound under this subset is a compound of formula I wherein $R^4$ is methyl, X is cyclopropyl and Y is methyl, and the compound is 1-cyclopropyl-3-hydroxy-N,N,6-trimethyl-4-oxo-1,4-dihydropyridine-2-carboxamide.

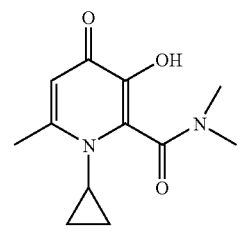

The most preferred compounds of this invention are compound IA, a compound of formula I wherein $R^3$=H; $R^4$=methyl, with the proviso that $R^1$=X=cyclopropyl; $R^2$=Y and Y is selected from the group consisting of $C_3$-$C_6$ cycloalkyl, $C_1$ to $C_6$ alkyl, and $C_1$ to $C_6$ alkyl monosubstituted with a $C_3$-$C_6$ cycloalkyl; or $R^1$=X=cyclopropyl, and $R^2R^5N$ when taken together form a heterocyclic ring selected from piperidinyl, morpholinyl, pyrrolidinyl or piperazinyl, wherein the group piperidinyl, morpholinyl, pyrrolidinyl or piperazinyl is either unsubstituted or substituted with one to three $C_1$-$C_6$ alkyl groups.

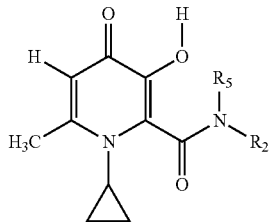

IA

In light of the above, the present invention provides a cycloalkyl derivative of 3-hydroxy-4-pyridinone having improved properties as compared to compounds reported in the prior art. The cycloalkyl group is attached to the N1 and/or C2 amido N atom. Prior to this application, compounds with N1-cycloalkyl substituent or C2 amido N-cycloalkyl substituent were unknown in the literature. These compounds are not prodrugs and have excellent metal ion selectivity. They show no complexation with essential metals such as calcium and magnesium at pH 7.4 in chemical assays. The $D_{7.4}$ value is within the range of an established drug deferiprone and the compound is orally active in the iron overload rat model. These compounds are designed with favorable phenolic C3 OH pKas in the range of 8.3 to 8.8, a $pFe^{3+}$ value of above 20, a smooth 1:3 ferric chelate formation as evident by Job's plot, and a $D_{7.4}$ value>0.1. The single crystal structure of the Fe(III) chelate confirms that the compound of formula I is a bidentate ligand.

BRIEF REFERENCE TO THE DRAWINGS

Figure 1:
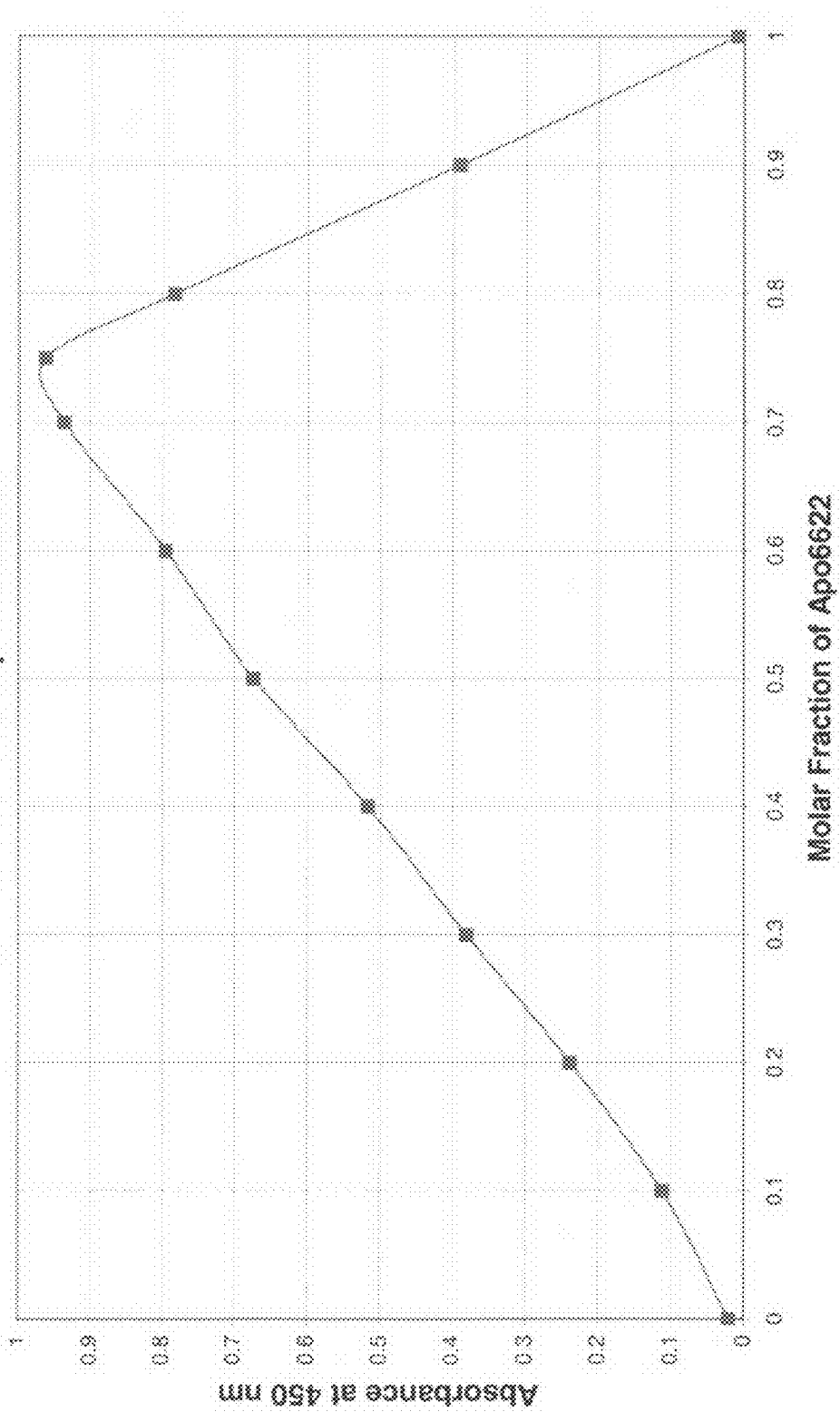

FIG. 1: is a diagrammatic representation of Job's plot of Apo6622 (1-cyclopropyl-3-hydroxy-6-methyl-4-oxo-1,4-dihydro-pyridine-2-carboxylic acid cyclopropylamide), a compound of formula I.

FIG. 2: is a diagrammatic representation of Job's plot of Apo6617 (1,6-dimethyl-3-hydroxy-4-oxo-1,4-dihydro-pyridine-2-carboxylic acid cyclopropylamide), a compound of formula I.

FIG. 3: is a diagrammatic representation of Job's plot of Apo6619 (1-cyclopropyl-3-hydroxy-6-methyl-4-oxo-1,4-dihydro-pyridine-2-carboxylic acid methylamide), a compound of formula I.

Figure 4:
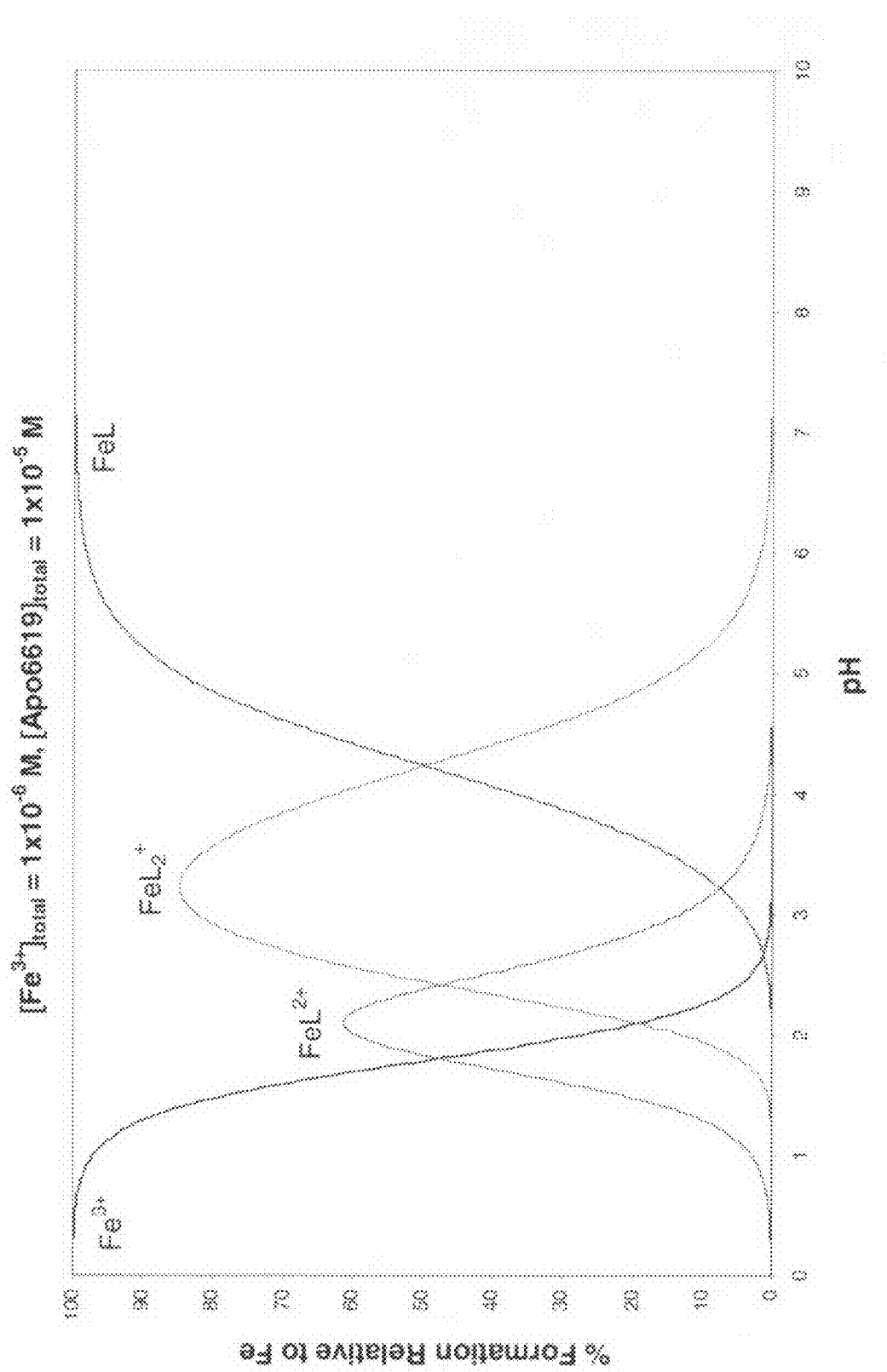

FIG. 4: is a speciation plot for $Fe^{3+}$-Apo6619.

Figure 5:
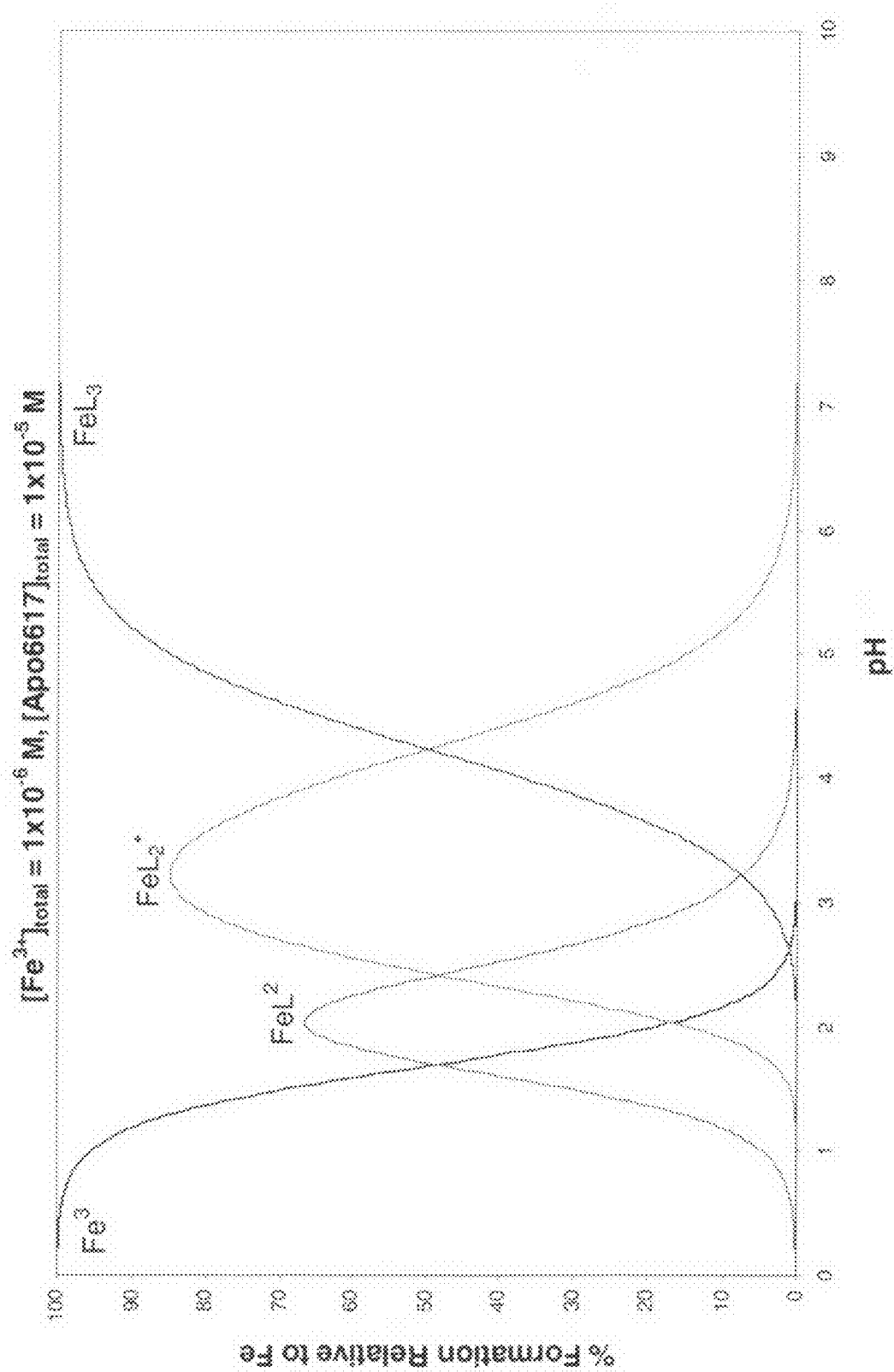

FIG. 5: is a speciation plot for $Fe^{3+}$-Apo6617.

Figure 6:
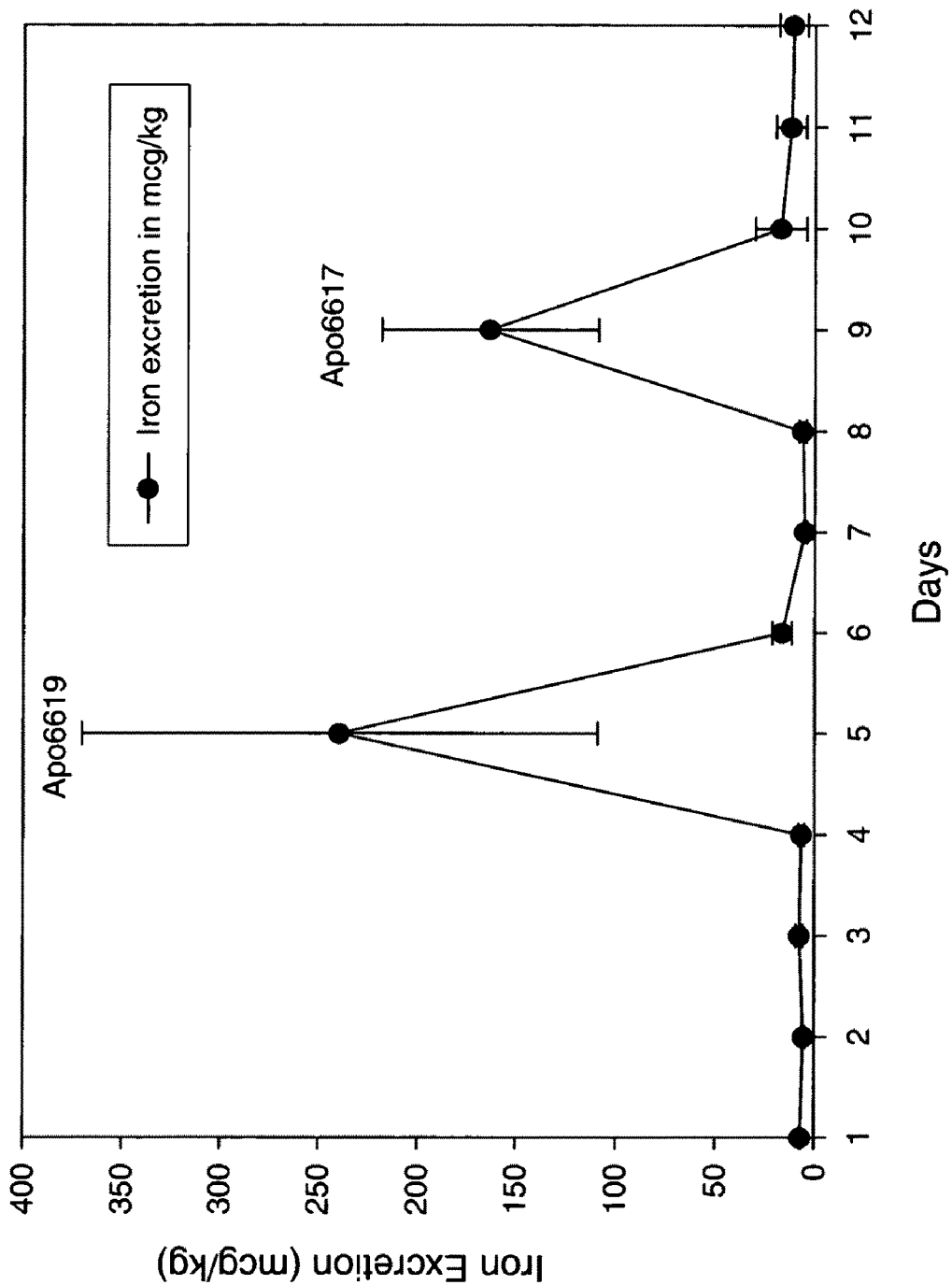

FIG. 6: is a graph demonstrating the effectiveness of Apo6619 and Apo6617 in Promoting Urinary Iron Excretion in the Iron Overloaded Rat (n=6).

FIG. 7: illustrates the single crystal structure of Fe(Apo6617)$_3$ chelate.

FIG. 8: illustrates the single crystal structure of Fe(Apo6619)$_3$ chelate.

FIG. 9: is a cyclic voltammogram of Fe-Apo6619 system at pH 7.4.

BRIEF REFERENCE TO THE TABLES

TABLE 1: Provides the chemical properties of compound of formula I.

TABLE 2: Demonstrates the metal binding selectivity of Apo6619.

TABLE 3: Demonstrates effectiveness of Apo6619 and Apo6617 in Promoting Fecal Iron Excretion in the Iron Overloaded Rat (n=6). Values are expressed as μg/day/kg.

TABLE 4: Demonstrates effectiveness of Apo6619 and Apo6617 in Promoting Urinary and Fecal Iron Excretion in the Iron Overloaded Rats (n=6/group). Values are expressed as μg/day/kg. Fecal excretion values 3 days after chelator administration are given and compared to the baseline values determined 3 days prior to chelator administration. Values are expressed as mean±1 SD.

TABLE 5: Provides the crystal data and structure refinement for Fe(Apo6617)$_3$.

TABLE 6: Provides the bond lengths [Å] and angles [°] for Fe(Apo6617)$_3$.

TABLE 7: Provides the crystal data and structure refinement for Fe(Apo6619)$_3$.

TABLE 8: Provides the bond lengths [Å] and angles [°] for Fe(Apo6619)$_3$.

DETAILED DESCRIPTION OF THE INVENTION

As used herein:

Alkyl means a branched or unbranched saturated hydrocarbon chain having, unless otherwise noted, one to six carbon atoms, including but not limited to methyl, ethyl, propyl, isopropyl, n-propyl, butyl, sec-butyl, isobutyl, n-pentyl, hexyl.

The term "cycloalkyl" as employed herein alone or as part of another group includes saturated cyclic hydrocarbon groups containing 1 ring, including monocyclic alkyl, containing a total of 3 to 6 carbons forming the ring, which includes cyclopropyl, cyclobutyl, cyclopentyl and cyclohexyl.

Pharmaceutically acceptable, non-toxic salts refer to pharmaceutically acceptable salts of the compounds of this invention, which retains the biological activity of the parent compounds and are not biologically or otherwise undesirable (e.g. the salts are stable). Salts of the two types may be formed from the compounds of this invention: (1) Salts of inorganic and organic bases from compounds of formula I, which has a phenol functional group, and (2) Acid addition salts may be formed at the amine functional group of compounds of formula I of this invention.

Pharmaceutically acceptable salts derived from inorganic bases include sodium, potassium, lithium, ammonium, calcium, and magnesium salts. Particularly preferred are the sodium, calcium and magnesium salts. Pharmaceutically acceptable, non-toxic salts derived from organic bases include salts of primary, secondary and tertiary amines, substituted amines including naturally occurring substituted amines, cyclic amines and basic ion exchange resins. Such salts are exemplified by, for example, 2-amino-2-hydroxymethyl propane 1,3-diol, isopropopylamine, tromethamine, glucosamine, methylglucamine, purines, piperazine, piperidine, N-ethylpiperidine, polyamine resins and the like.

Pharmaceutically acceptable acid addition salts are formed with inorganic and organic acids such as halo acids, sulfuric acid, nitric acid, phosphoric acid, methanesulfonic acid, and ethanesulfonic acid.

The compounds of this invention are 2-amido derivatives of 4-oxo-1,4-dihydropyridine-2-carboxamide derivatives having the general structure:

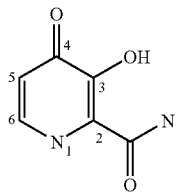

Most compounds are named as a derivative of 4-oxo-1,4-dihydropyridine-2-carboxamide, for example:
1-cyclopropyl-N-hexyl-3-hydroxy-6-methyl-4-oxo-1,4-dihydropyridine-2-carboxamide:

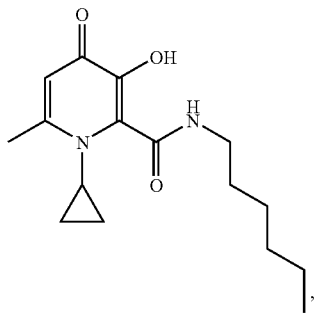

N-cyclohexyl-1-cyclopropyl-3-hydroxy-6-methyl-4-oxo-1,4-dihydropyridine-2-carboxamide:

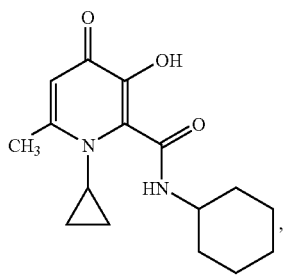

N-(cyclohexylmethyl)-1-cyclopropyl-3-hydroxy-6-methyl-4-oxo-1,4-dihydropyridine-2-carboxamide:

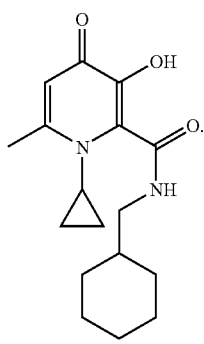

In some cases, the compounds are named using "pyridin-4(1H)-one" as the basic skeleton. Examples are:
1-cyclopropyl-3-hydroxy-6-methyl-2-(morpholin-4-ylcarbonyl)pyridin-4(1H)-one:

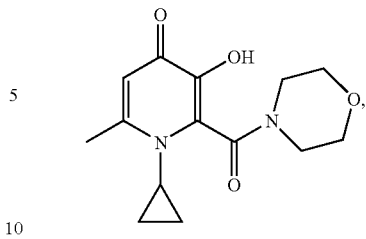

1-cyclopropyl-3-hydroxy-6-methyl-2-[(4-methylpiperazin-1-yl)carbonyl]pyridin-4(1H)-one:

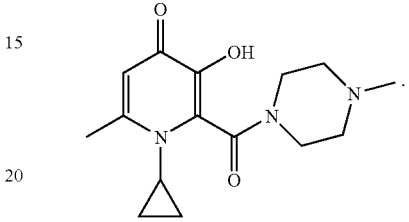

The term "animals" refers to humans as well as all other animal species, particularly mammals (e.g. dogs, cats, horses, cattle, pigs, etc.), reptiles, fish, insects and helminths.

Compounds of this invention are designed to improve properties to known deferiprone analogues. One criteria used in the design rationale of oral active chelators in the 3-hydroxy-4-pyridinone series are compounds having $pFe^{3+}$ values higher than deferiprone ($pFe^{3+}=19.7$). The definition of $pFe^{3+}$ used herein is the concentration of ferric ion in solution when the total amount of iron equals $10^{-6}$ M and the concentration of ligand is $10^{-5}$ M and pH is 7.4. It is calculated using experimental determined pKa and metal complexation constants using Hyperquad software (Version 2.1, Peter Gans, University of Leeds). The lowering of the pKa value of the C3 phenolic OH to less than 8.8 ensures that a higher $pFe^{3+}$ value when combined with a favorable complexation constant $\beta_3$. The concept of complexation is detailed below.

The stepwise and overall complexation constants of a bidentate ligand such as 3-hydroxy-4-pyridinone follow:

Fe(III)+Ligand→Fe[Ligand]$_1$K$_1$

Fe[Ligand]$_1$+Ligand→Fe[Ligand]$_2$K$_2$

Fe[Ligand]$_2$+Ligand→Fe[Ligand]$_3$K$_3$

Complexation constant $\beta_3$=K$_1$.K$_2$.K$_3$

The iron chelator drug deferiprone (1,2-dimethyl-3-hydroxy-4-pyridinone) chelates iron with a complexation constants (log $\beta_3$) of 36.3 and a $pFe^{3+}$ of 19.7. The pKas of deferiprone is 3.56 and 9.64. Most compounds of this invention have similar complexation constants (log $\beta_3$) in the range of 34 to 36, a $pFe^{3+}>20$ and favorable phenol pKa values of 8.3 to 8.8. Accordingly, compounds of this invention are excellent chelators of Fe(III). The theoretically calculated human jejunum effective permeability [$P_{eff}$] of compounds of this invention is predicted by computational calculations using QMPRPlus™ software (from Simulationplus inc.). Most compounds of this invention have calculated $P_{eff}$ in the range of $1\pm0.3$ (cm/s×$10^{-4}$), implying that the compounds have good human jejunal permeability. The chemical properties of representative compounds of formula I are shown in Table 1.

Significantly, compounds of formula I with cycloalkyl groups at R$^1$ and/or R$^2$ are metal chelators with high $pFe^{3+}$ values. The $D_{7.4}$ values of compounds of formula I are similar to deferiprone and further studies in iron overload rats showed that compounds of formula I are effective in the removal of iron in vivo. The details of the animal efficacy study are shown in the examples below.

Compounds of formula I do not bind essential metals such as manganese, calcium and magnesium. The pM values and complexation constants of a representative compound of formula I are shown in Table 2 (and discussed in more detail in Example 11). The compound has preference for binding $Fe^{3+}$ over other bivalent and trivalent metals such as Cu, Zn and Al.

Compounds of formula I are novel cycloalkyl derivatives of 3-hydroxy-4-pyridinones. They have $pFe^{3+}$ values above 20, a favorable $D_{7.4}$ value comparable to deferiprone, a preference towards the chelation of $Fe^{3+}$ and a C2-alkylcarbamoyl or C2-cycloalkylcarbamoyl moiety that is designed to block the phase II metabolism of the 3-OH group.

In addition to the above, compounds of formula I binds $Fe^{3+}$ in the ratio of 1:3 at physiological conditions at pH 7.4. The Job's plot analysis confirms the 1:3 ratio of chelator to ferric metal (FIG. (1 to 3) and Example 9).

The speciation plots of the Fe-complex vs. different pHs can be calculated by using Hyperquad Stimulation and Speciation software (HYSS2© 2000 Protonic Sofware) with the input of experimental pkas (example 10 and 11) and the complexation constants $K_1$, $K_2$ and $K_3$ (Example 14). FIGS. 4 and 5 illustrate the speciation plot of compounds of formula I at different pHs. In both studies, representative compounds of formula I exclusively form $FeL_3$ chelates at pH above 7.0 (where L is a bidentate ligand), thus ensuring no presence of $FeL^{2+}$ or $FeL^{2+}$ species at physiological pH. The absence of these species ensures that there is no exposed iron in vivo at the physiological pH of 7.4.

Compounds of formula I wherein $R^1$ is X with the proviso that $R^2$ is Y; or $R^1$ is T with the proviso that $R^2$ is W is prepared according to the method outlined in Scheme 1.

Acid (II) is reacted with 1,1'-carbonyldiimdazole in an inert solvent for 2 to 5 hrs, preferably 5 hrs in an inert solvent at temperatures between 30 to 70° C. Followed by the addition of an amine $R^2R^5NH$, the compound (III) is isolated by conventional means. A solution of (III) and an amine $R^1NH^2$ in an inert solvent such as an alcohol is heated at 50 to 80° C. to effect the amine insertion of (III) for a period of 3 to 48 hrs to give compound (IV). An alternate method for the preparation of compound (IV) involves the reaction of a compound of formula (II) with an amine $R^1NH^2$ in an inert solvent to give the acid of formula (V). Compound (V) is then reacted with thionyl chloride and dimethylformamide to give a compound of formula (IV). The compound is isolated by traditional means e.g. column chromatography and crystallization. Hydrogenation of compound (IV) in alcohol over a hydrogenation catalyst affords compound (I), which is isolated by conventional means. The preferred hydrogenation catalyst is palladium on carbon or palladium hydroxide on carbon and Raney Ni. The preparation of the starting material acid (II) is reported in U.S. Pat. No. 6,426,418. A general procedure for the preparation of an acid of formula (V) can be found in CA 2379370.

Compounds of formula I were tested in iron overloaded rats. The fecal iron excretion and urinary excretion data for representative compounds Apo6617 and Apo6619 are shown in Tables 3 and 4, and FIG. 6, respectively. Both compounds showed significant fecal iron excretion when compared to control at an oral dose of 113 and 450 μmol/kg. Further, Apo6619 and Apo6617 facilitate the urinary excretion of iron significantly higher than deferiprone at 450 μmol/kg. Both compounds are considered more potent than deferiprone in iron mobilization in iron overloaded rats.

The ferric chelate of compounds of formula I have been synthesized and isolated (Example 16). The single crystal Scheme 1

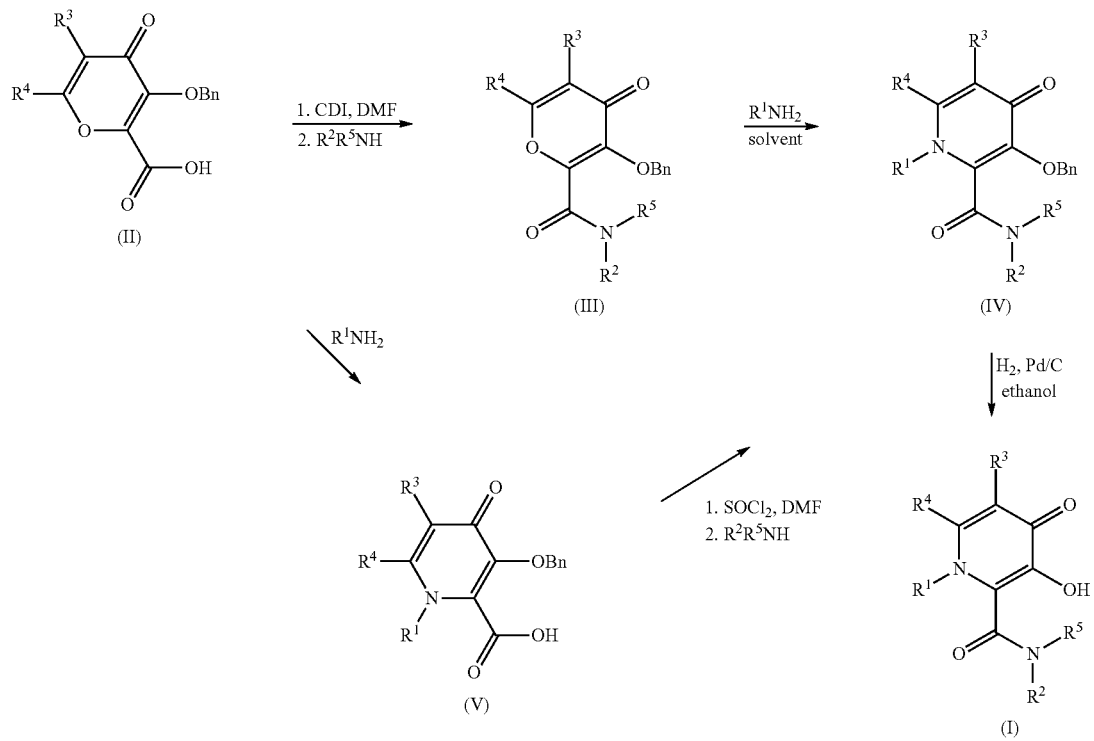

structures of Fe(Apo6617)$_3$ and Fe(Apo6619)$_3$ definitively prove that these bidentate compounds reacted with Fe(III) to give a 1:3 trisbidentate chelate (Table 5 to 8, FIG. 7-8).

Another criteria in the design of compounds of formula I concerns controlling the redox potential of the Fe-chelate system at pH 7.4 to a negative value below −320 mv (vs NHE) to prevent any reactions with oxygen species. Iron exists in multiple states including Fe$^{2+}$ and Fe$^{3+}$. The iron (II)/iron (III) pair can act as a pair of one electron reducing agent and oxidizing agent. According to Crumbliss (http://www.medicine.uiowa.edu/FRRBNirtualSchool/Crumbliss-Fe.pdf) and Pierre (BioMetals, 12, 195-199, 1999), selective chelation of iron with redox potential control is a means to prevent iron from participating in a catalytic cycle to produce toxic hydroxyl radicals and/or reactive oxygen species (ROS) (e.g. via the Fenton reaction or Haber Weiss cycle). The Fe (III)-trischelate system with redox potential below −320 mv (vs NHE or −540 mv vs Ag/AgCl) at pH 7.4 will not be reduced by any biological reducing agents such as NADPH/NADH, therefore it will not participate in the Haber Weiss cycle to generate ROS (reactive oxygen species). Within the mammalian body, iron is bound to different proteins such as transferrin in human blood to ensure it remains in a form that cannot react with any oxygen molecules. The $E_{1/2}$ value of Fe-transferrin is −500 mv (vs. NHE or −720 mv vs. Ag/AgCl).

The redox potential of iron complexes can be measured by cyclic voltammetry (CV). The use of CV to measure the redox potentials of iron chelates deferiprone, deferrioxamine and Apo6619 (a representative compound of this invention) as chelators respectively, is illustrated in Example 17 below. Iron chelates such as Fe-desferrioxamine (DFO) and Fe-(deferiprone)$_3$ have redox potential $E_{1/2}$ values at −698 mv (vs Ag/AgCl) and −834 mv (vs. Ag/AgCl) at pH 7.4 respectively. Compounds of formula I such Fe(Apo6619)$_3$ has a $E_{1/2}$ value of −691 mv (vs. Ag/AgCl) similar to that of desferrioxamine. The cyclic voltammogram of Fe-DFO, Fe(deferiprone)$_3$ and Fe(Apo6619)$_3$ can be found in FIG. 9. One advantage of the chelators of this invention is that the redox potentials of their iron chelates lie in the extreme negative range at physiological pH 7.4, therefore their iron chelates will not participate in the redox cycle to generate reactive oxygen species at physiological pH. When combined with other novel properties as described in this invention, the compounds of formula I are effective agents in the removal of iron via a chelation mechanism.

For the treatment of iron overloaded diseases such as thalassemia, sickle cell disease, haemochromatosis and the treatment of patients having a toxic concentration of iron, the compounds of the invention may be administered orally, topically, or parenterally in dosage unit formulations containing conventional non-toxic pharmaceutically acceptable carriers, adjuvants and vehicles.

For the treatment of non-iron overloaded conditions such as HIV infection, protective effect against anthracycline cardiac poisoning, cancer and malaria, the compounds of this invention may also be administered orally, topically, or parenterally in dosage unit formulations containing conventional non-toxic pharmaceutically acceptable carriers, adjuvants and vehicles.

The term parenteral as used herein includes subcutaneous injection or infusion techniques. In addition to the treatment of warm-blooded animals such as mice, rats, horses, cattle, sheep, dogs, cats, etc., the compounds of the invention are effective in the treatment of humans.

For use in pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as a liquid. Pharmaceutically administrable compositions can, for example, be prepared by dissolving, dispersing, etc. an active compound as defined above and optional pharmaceutically adjuvants in a carrier, such as, for example, water, saline, aqueous dextrose, glycerol, ethanol, and the like, to thereby form a solution or suspension. If desired, the pharmaceutical composition to be administered may also contain a minor amount of non-toxic auxiliary substances such as wetting or emulsifying agents and the like, for example, sodium acetate, sorbitan monolaurate, triethanolamine sodium acetate, triethanol-amine oleate, etc. Actual methods of preparing such dosage forms are known, or will be apparent to those skilled in this art: for example, see Remington's Pharmaceutical Sciences, Mack Publishing Company, Easton, Pa., 15th Edition, 1975, ch. 83 p. 1436-1460, and ch. 89 p. 1576-1607. The composition of formulation to be administered will, in any event, contain a quantity of the active compound(s) in an amount effective to alleviate the symptoms of the subject being treated.

The pharmaceutical compositions containing the active ingredient may be in a form suitable for oral use, for example, as tablets, troches, lozenges, aqueous or oily suspensions, dispersible powders or granules, emulsions, hard and soft capsules, or syrups or elixirs. Compositions intended for oral use may be prepared according to any method known to the art for the manufacture of pharmaceutical compositions and such compositions contain one or more agents from the group consisting of sweetening agents, flavoring agents, coloring agents and preserving agents in order to provide pharmaceutically elegant and palatable preparations. Tablets contain the active ingredient in admixture with the non-toxic pharmaceutically acceptable excipients, which are suitable for the manufacture of tablets. The excipients may be for example, inert diluents, such as calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be coated by known techniques to delay the disintegration and absorption in the gastrointestinal tract and thereby provide a sustained action over a long period. For emollient, emulsifier, or moisturer, monostearate or glyceryl distearate may be employed.

Formulations for oral use may also be presented as hard gelatin capsules wherein the active ingredients are mixed with an inert solid diluent, for example, calcium phosphate or kaolin, or as soft gelatin capsules wherein the active ingredient is mixed with water or an oil medium, for example peanut oil, liquid paraffin, or olive oil.

Aqueous suspensions can contain the active materials in an admixture with the excipient suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum and gum acacia; dispersing or wetting agents may be a naturally-occurring phosphate, for example lecithin, or condensation products of an alkene oxide with fatty acids, for example polyoxyethylene stearate, or condensation products of ethylene oxide with long chain aliphatic alcohols, for example heptadecathyl-eneoxycetanol, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, such as sucrose or saccharin.

Oily suspensions may be formulated by suspending the active ingredient in a vegetable oil, for example rachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with the dispersing or wetting agent, suspending agent and one or more preservatives. Suitable dispersing or wetting agents and suspending agents are exemplified by those already mentioned above. Additional recipients, for example sweetening, flavoring and coloring agents, may also be present.

The pharmaceutical composition of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring phosphates, esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents.

Syrups and elixirs may be formulated with sweetening agents, for example glycerol, propylene glycol, orbital or sucrose. Such formulations may also contain a demulcent, a preservative and flavoring and coloring agents. The pharmaceutical compositions may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solutions and isotonic sodium chloride solution. In addition, fixed oils are conventionally employed as a solvent or suspending medium. For this purpose any bland fixed oil may be employed including synthetic mono- or diglycerides. In addition, fatty acids such as oleic acid find use in the preparation or injectables.

Compounds of formula (I), or if appropriate a pharmaceutically-acceptable salt thereof and/or a pharmaceutically-acceptable solvate thereof, may also be administered as a topical formulation in combination with conventional topical excipients. Examples of topical formulations are ointments, creams or lotions, impregnated dressings, gels, gel sticks, spray and aerosols. The formulations may contain appropriate conventional additives such as preservatives, solvents to assist drug penetration and emollients in ointments and creams. They may also contain compatible conventional carriers, such as cream or ointment bases and ethanol or oleyl alcohol for lotions. Topical formulations are envisaged where appropriate, to contain an amount of actives to alleviate the symptoms of the subject being treated. Suitably, the compound of formula (I), or if appropriate a pharmaceutically-acceptable salt thereof, will compromise from about 0.5 to 10% by weight of the formulation. Suitable cream, lotion, gel, stick, ointment, spray or aerosol formulations that may be used for compounds of formula (I) or if appropriate a pharmaceutically-acceptable salt thereof, are conventional formulations well known in the art, for example, as described in standard text books Remington's Pharmaceutical Sciences, Mack Publishing Company, Easton, Pa., 15th Edition, 1975, ch. 83 p. 1436-1460, and ch. 89 p. 1576-1607.

Parenteral administration is generally characterized by injection, either subcutaneously, intramuscularly or intravenously. Injectables can be prepared in conventional forms, either as liquid solutions or suspension in liquid prior to injection, or as emulsions. Suitable excipients are for example, water, saline, dextrose, glycerol, ethanol or the like. In addition, if desired, the pharmaceutical compositions to be administered may also contain minor amounts of non-toxic auxiliary substance such as wetting or emulsifying agents, pH buffering agents and the like, such as for example, sodium acetate, sorbitan monolaurate, triethanolamine oleate, etc.

The amount of active ingredient that may be combined with the carrier materials to produce a single dosage form will vary depending upon the host treated, and the particular mode of administration of humans may contain from 0.5 mg to 5 gm of active agent compounded with an appropriate and convent amount of carrier material which may vary from about 5 to about 95% of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, drug combination and the severity of the particular disease undergoing therapy.

The compounds of the present invention differ from those compounds reported in U.S. Pat. No. 6,448,273, U.S. Pat. No. 6,335,353, RE 35,948 and U.S. Pat. No. 5,688,815. The first three patents describe 3-hydroxy-4-pyridinones having a N1 aliphatic hydrocarbon group. U.S. Pat. No. 5,688,815 also describes 3-hydroxy-4-pyridinones with a N1 substituted or unsubstituted lower alkyl group. According to a standard chemistry textbook, Organic Chemistry by James B. Hendrickson, Donald J. Cram, George S. Hammond, third edition, 1970, McGraw Hill, p. 72, aliphatic hydrocarbons are composed of chains of carbon atoms not arranged in rings. Substances belonging to this group are sometimes referred as open chain compounds. Examples of aliphatic hydrocarbon group are linear or branched alkyls such as methyl, ethyl, propyl, isopropyl, isobutyl, butyl and tert-butyl. The compounds of this invention consist of 3-hydroxy-4-pyridinones with (a) N1-cycloalkyl substituent and C2 cycloalkylcarbamoyl substituent; or (b) N1-cycloalkyl substituent and C2 cycloalkylcarbamoyl substituent; or (c) N1-alkyl substituent with C2 cycloalkyl-carbamoyl substituent. They are compounds with acyclic hydrocarbon substituents. In acyclic hydrocarbons, the carbon chains form rings. Examples of acyclic hydrocarbon groups are cycloalkyl derivatives such as cyclopropyl, cyclobutyl, cyclopentyl and cyclohexyl. The four patents, U.S. Pat. No. 6,448,273, U.S. Pat. No. 6,335, 353, RE 35,948 and U.S. Pat. No. 5,688,815 do not cover cycloalkyl derivatives of 3-hydroxy-4-pyridinones. This invention covers 3-hydroxy-4-pyridinones with a N1-cycloalkyl group with an alkylcarbamoyl group at C2 or a cycloalkylcarbamoyl group at C2. It also covers 3-hydroxy-4-pyridinones with a cycloalkylcarbamoyl group at C2 with a N1-alkyl group.

The invention is further described and illustrated in the following specific examples.

SPECIFIC DESCRIPTION OF THE MOST PREFERRED EMBODIMENTS

Example 1

Preparation of 3-Benzyloxy-6-methyl-4-oxo-4H-pyran-2-carboxylic Acid Cyclohexylamide 1,1'-carbonyldiimidazole (1.99 g, 12.30 mmol) was added to a solution of the 3-(benzyloxy)-6-methyl-4-oxo-4H-pyran-2-carboxylic acid (2.0 g, 7.69 mmol) in dimethylformamide (DMF, 18 ml) at room temperature. The resulting solution was heated at 40°-50° C. for 3 hrs. A light yellow solution was observed. Cyclohexylamine (1.23 ml, 10.76 mmol) was then added. The resulting mixture was stirred at room temperature for overnight. The DMF was removed under reduced pressure to give light yellow oil as a crude product, which was purified by flash column chromatography (elution gradient: from 1:1 ethyl acetate/hexane to 10% methanol in ethyl acetate) to yield the titled compound (1.60 g, yield 61%) as white solid.

M.p. 118-120° C.; $^1$H-NMR (CDCl$_3$, 400 MHz) δ 0.91 (m, 2H, cyclohexyl-H), 1.29 (m, 2H, cyclohexyl-H), 1.58 (m, 3H, cyclohexyl-H), 1.79 (m, 2H, cyclohexyl-H), 2.37 (s, 3H, CH$_3$), 3.79 (m, 1H, CH), 5.40 (s, 2H, CH$_2$), 6.28 (s, 1H, CH), 7.41 (m, 5H, ArH), 7.67 (br, 1H, NH); MS (m/z) 342 (M$^+$+1).

In a similar manner to that described above, by substituting cyclohexylamine with other amine, the following compounds are prepared:

3-Benzyloxy-6-methyl-4-oxo-4H-pyran-2-carboxylic Acid Cyclopropylamide

M.p. 79-80° C.; $^1$H-NMR (CDCl$_3$, 400 MHz) δ 0.21 (m, 2H, cyclopropyl-H), 0.70 (m, 2H, cyclopropyl-H), 2.35 (s, 3H, CH$_3$), 2.71 (m, 1H, CH), 5.35 (s, 2H, CH$_2$), 6.27 (s, 1H, CH), 7.39 (m, 5H, ArH), 7.70 (s, 1H, NH); 13C (CDCl$_3$) δ 6.35, 7.21, 19.87, 22.61, 22.70, 75.56, 115.37, 128.94 (2C), 129.17 (2C), 129.25, 135.49, 146.14, 146.39, 160.22, 165.74, 176.17; MS (m/z) 300 (M$^+$+1).

3-Benzyloxy-6-methyl-4-oxo-4H-pyran-2-carboxylic Acid Methylamide

M.p. 137-140° C., $^1$H-NMR (CDCl$_3$, 400 MHz) δ 2.38 (s, 3H, CH$_3$), 2.78 (d, 3H, NCH$_3$), 5.39 (s, 2H, CH$_2$), 6.30 (s, 1H, CH), 7.40 (m, 5H, ArH), 7.62 (br, 1H, NH); MS (m/z) 300 (M$^+$+1).

Example 2

Preparation of 3-Benzyloxy-1,6-dimethyl-4-oxo-1,4-dihydro-pyridine-2-carboxylic Acid Cyclohexylamide To a solution of 3-benzyloxy-6-methyl-4-oxo-4H-pyran-2-carboxylic acid cyclohexylamide (1.40 g, 4.1 mmol) in 5 ml of methanol, methylamine solution (9 ml of 2M solution in methanol, 16 mmol) was added. The resulting solution was stirred at 70 to 75° C. for overnight under the pressure in a sealed tube. The solvent was removed under reduced pressure gave light yellow solid as a crude product. The material was purified by column chromatography (elution gradient: 100% ethyl acetate to 25% methanol in ethyl acetate) to give the titled compound as white solid (1.20 g, 83.0%). M.p. 258-260° C.; $^1$H-NMR (CDCl$_3$, 400 MHz) δ 1.26-1.45 (m, 6H, cyclohexyl-H), 1.79 (m, 2H, cyclohexyl-H), 1.95 (m, 2H, cyclohexyl-H), 2.41 (s, 3H, CH$_3$), 3.82 (s, 3H, NCH$_3$), 3.95 (m, 1H, CH), 5.13 (s, 2H, CH$_2$), 7.19 (s, 1H, CH), 7.36 (m, 3H, ArH), 7.43 (m, 2H, ArH), 8.50 (br, 1H, NH); MS (m/z) 355 (M$^+$+1).

In a similar manner, by substituting 3-benzyloxy-6-methyl-4-oxo-4H-pyran-2-carboxylic acid cyclohexylamide with other 3-benzyloxy-6-methyl-4-oxo-4H-pyran-2-carboxylic acid amide derivatives, the following compounds are prepared:

3-benzyloxy-1,6-dimethyl-4-oxo-1,4-dihydro-pyridine-2-carboxylic Acid Cyclopropylamide M.p. 187-189° C.; $_1$H-NMR (CDCl$_3$, 400 MHz) δ 0.52 (m, 2H, cyclopropyl-H), 0.74 (m, 2H, cyclopropyl-H), 2.18 (s, 3H, CH$_3$), 2.78 (m, 1H, CH), 3.50 (s, 3H, NCH$_3$), 5.08 (s, 2H, CH$_2$), 6.12 (s, 1H, CH), 7.33 (m, 3H, ArH), 7.39 (m, 2H, ArH), 7.91 (br, 1H, NH); MS (m/z) 313 (M$^+$+1).

3-Benzyloxy-1-cyclopropyl-6-methyl-4-oxo-1,4-dihydro-pyridine-2-carboxylic Acid Methylamide M.p. 132-135° C.; $^1$H-NMR (CDCl$_3$, 400 MHz) δ 1.05 (m, 4H, cyclopropyl-H), 2.38 (s, 3H, CH$_3$), 2.70 (d, J=1.8 Hz, 3H, NCH$_3$), 3.35 (m, 1H, CH), 5.07 (s, 2H, CH$_2$), 6.14 (s, 1H, CH), 7.15 (br., 1H), 7.35 (m, 5H, ArH); $^{13}$C (CDCl$_3$) δ 9.48, 20.30, 25.86, 34.15, 74.01, 118.16, 127.79, 128.06 (2C), 128.22 (2C), 137.35, 142.05, 143.98, 149.91, 162.01, 173.89; MS (m/z) 313 (M$^+$+1).

3-Benzyloxy-1-cyclopropyl-6-methyl-4-oxo-1,4-dihydro-pyridine-2-carboxylic Acid Cyclopropylamide M.p. 164-167° C.; $^1$H-NMR (CDCl$_3$, 400 MHz) δ 0.54 (m, 2H, cyclopropyl-H), 0.76 (m, 2H, cyclopropyl-H), 1.08-1.11 (m, 4H, cyclopropyl-H), 2.35 (s, 3H, CH$_3$), 2.75 (m, 1H, CH), 3.37 (m, 1H, CH), 5.05 (s, 2H, CH$_2$), 6.13 (s, 1H, CH), 7.33 (m, 5H, ArH), 7.89 (br, s, 1H, NH); MS (m/z) 339 (M$^+$+1).

Example 3

3-Hydroxy-1,6-dimethyl-4-oxo-1,4-dihydro-pyridine-2-carboxylic Acid Cyclohexylamide [Apo6621]

Pd(OH)$_2$ on charcoal (0.18 g, 10% w dry basis) was added to a solution of 3-benzyloxy-1,6-dimethyl-4-oxo-1,4-dihydro-pyridine-2-carboxylic acid cyclohexylamide (1.0 g, 2.82 mmol) in ethanol (50 ml) under nitrogen. The mixture was hydrogenated at 50 psi for 4 hrs. The Pd(OH)$_2$ was removed by filtration through a layer of Celite®, the Celite® cake was then washed with ethanol (3×10 ml). The ethanol filtrate was evaporated to give an off-white solid (0.57 g, 77%). Further purification by recrystallization from methanol (15 ml) gave the title compound as a white solid (0.18 g). M.p. 280-285° C. (dec); $^1$H-NMR (CD$_3$OD 400 MHz) δ 1.30-1.43 (m, 5H, cyclohexyl-H), 1.70 (m, 1H, cyclohexyl-H), 1.80 (m, 2H, cyclohexyl-H), 2.00 (m, 2H, cyclohexyl-H), 2.41 (s, 3H, CH$_3$), 3.63 (s, 3H, CH$_3$), 3.90 (m, 1H, CH), 6.38 (s, 1H, CH); MS (m/z) 265 (M$^+$+1).

In a similar manner, by substituting 3-benzyloxy-1,6-dimethyl-4-oxo-1,4-dihydro-pyridine-2-carboxylic acid cyclohexylamide with other 3-benzyloxy-4-oxo-1,4-dihydro-pyridine-2-carboxylic acid cycloalkyl amides, the following compounds are prepared:

3-Hydroxy-1,6-dimethyl-4-oxo-1,4-dihydro-pyridine-2-carboxylic Acid Cyclopropylamide [Apo6617]

M.p. 260-262° C.; $^1$H-NMR (MeOD-$d_4$, 400 MHz) δ 0.66 (m, 2H, cyclopropyl-H), 0.85 (m, 2H, cyclopropyl-H), 2.41 (s, 3H, $CH_3$), 2.95 (m, 1H, CH), 3.63 (m, 1H, $NCH_3$), 6.38 (s, 1H, CH); MS (m/z) 223 ($M^+$+1).

1-Cyclopropyl-3-hydroxy-6-methyl-4-oxo-1,4-dihydro-pyridine-2-carboxylic Acid Methylamide [Apo6619]

M.p. 258-260° C. (dec); $^1$H-NMR (MeOD-$d_4$, 400 MHz) δ 1.05 (m, 2H, cyclopropyl-H), 1.19 (m, 2H, cyclopropyl-H), 2.54 (s, 3H, $CH_3$), 2.97 (s, 1H, $NCH_3$), 3.46 (m, 1H, CH), 6.33 (s, 1H, CH); MS (m/z) 223 ($M^+$+1).

Example 4

Preparation of 3-(benzyloxy)-N-cyclobutyl-6-methyl-4-oxo-4H-pyran-2-carboxamide A mixture of 3-(benzyloxy)-6-methyl-4-oxo-4H-pyran-2-carboxylic acid (2.5 g, 9.6 mmol, 1.0 equiv), 1,1'-carbonyldiimidazole (2.49 g, 15.37 mmol, 1.6 equiv) in DMF (20 mL) was stirred at 50° C. for 5 h. The mixture was cooled to room temperature. Cyclobutylamine hydrochloride (1.24 g, 11.52 mmol, 1.2 equiv) and $Et_3N$ (1.74 mL, 12.48 mmol, 1.3 equiv) was added, and the mixture was stirred overnight at room temperature. The solvent was removed under reduced pressure. Purification by chromatography (1:1 hexanes/EtOAc, then EtOAc) provided the titled compound (2.76 g, 91.56%) as a yellow solid. M.p. 69.3-71.0° C.; $^1$H-NMR (CDCl$_3$, 400 MHz) δ 1.51-1.72 (m, 4H, cyclobutyl H), 2.19-2.28 (m, 2H, cyclobutyl H), 2.37 (s, 3H, $CH_3$), 4.39-4.41 (m, 1H, CH), 5.41 (s, 2H, $OCH_2Ph$), 6.30 (s, 1H, CH), 7.39-7.49 (m, 5H, ArH), 7.86 (br, 1H, NH), and MS (m/z) 314 ($M^+$+1), 217, 91.

Proceeding in a similar manner, the following compound is prepared:

3-(benzyloxy)-N-cyclopentyl-6-methyl-4-oxo-4H-pyran-2-carboxamide

M.p. 108.0-108.5° C.; $^1$H-NMR (CDCl$_3$, 400 MHz) δ 1.11-1.16 (m, 2H, cyclopentyl H), 1.50-1.55 (m, 4H, cyclopentyl H), 1.87-1.92 (m, 2H, cyclopentyl H), 2.38 (s, 3H, $CH_3$), 4.17-4.22 (m, 1H, CH), 5.41 (s, 2H, $CH_2$), 6.30 (s, 1H, CH), 7.38-7.43 (m, 5H, ArH), 7.72 (br, 1H, NH), MS (m/z) 328 ($M^+$+1), 217, 91.

Example 5

Preparation of 3-(benzyloxy)-N-cyclobutyl-1,6-dimethyl-4-oxo-1,4-dihydropyridine-2-carboxamide To a solution of the compound from example 4 (2.616 g, 8.35 mmol, 1.0 equiv) in methanol (10 ml) was quickly added methylamine (2M in methanol, 20 ml, 40 mmol, 4.79 equiv). The sealed tube was stirred overnight at 70-75° C. The resulting brown solution was evaporated to dryness and purified by chromatography (EtOAc, then 1:4 MeOH/EtOAc) provided the titled compound (1.70 g, 62.24%) as a white solid. M.p. 221.3-222.4° C.; $^1$H-NMR (DMSO-$d_6$, 400 MHz) δ 1.65-1.69 (m, 2H, cyclobutyl H), 1.90-1.95 (m, 2H, cyclobutyl H), 2.14-2.21 (m, 2H, cyclobutyl H), 2.31 (s, 3H, $CH_3$), 3.42 (s, 3H, $NCH_3$), 4.34-4.30 (m, 1H, CH), 5.05 (s, 2H, $OCH_2Ph$), 6.22 (s, 1H, CH), 7.39-7.30 (m, 5H, ArH), 9.08-9.06 (d, 1H, J=7.08 Hz, NH); MS (m/z) 327 ($M^+$+1), 230, 166, 91.

Proceeding in a similar manner, the following compound is prepared: 3-(benzyloxy)-N-cyclopentyl-1,6-dimethyl-4-oxo-1,4-dihydropyridine-2-carboxamide M.p. 233.6-234.4° C.; $^1$H-NMR (DMSO-$d_6$, 400 MHz) δ 1.43-1.52 (m, 4H, cyclopentyl H), 1.54-1.60 (m, 2H, cyclopentyl H), 1.78-1.83 (m, 2H, cyclopentyl H), 2.30 (s, 3H, $CH_3$), 3.43 (s, 3H, $NCH_3$), 4.13-4.18 (m, 1H, CH), 5.04 (s, 2H, $OCH_2Ph$), 6.22 (s, 1H, CH), 7.30-7.41 (m, 5H, ArH), 8.80-8.82 (d, J=6.95 Hz, 1H, NH); MS (m/z) 341 ($M^+$+1), 230, 166, 91.

Example 6

Preparation of N-cyclobutyl-3-hydroxy-1,6-dimethyl-4-oxo-1,4-dihydropyridine-2-carboxamide [Apo6622]

A mixture of N-cyclobutyl-3-benzyloxy-1,6-dimethyl-4-oxo-1,4-dihydropyridine-2-carboxamide (1.528 g, 4.68 mmol, 1.0 equiv), 10% Pd on activated carbon (200 mg, wet), and ethanol (200 ml) was stirred under 50 psi of $H_2$ at room temperature for 2.5 h. The catalyst was filtered through Celite® and the filtrate was evaporated to give a solid, which was recrystallized from MeOH gave the titled compound (0.57 g, 51.5%) as a white solid. M.p. 277.3° C. (dec); $^1$H-NMR (DMSO-$d_6$, 400 MHz) δ 1.68-1.70 (m, 2H, cyclobutyl H), 1.95-2.01 (m, 2H, cyclobutyl H), 2.20-2.26 (m, 2H, cyclobutyl H), 2.29 (s, 3H, $CH_3$), 3.41 (s, 3H, $NCH_3$), 4.31-4.35 (m, 1H, CH), 6.13 (s, 1H, CH), 8.98 (br, 1H, NH); MS (m/z) 237 ($M^+$+1), 185, 166, 123.

Proceeding in a similar manner, the following compounds are prepared:

N-cyclopentyl-3-hydroxy-1,6-dimethyl-4-oxo-1,4-dihydro-pyridine-2-carboxamide [Apo6620]

M.p. 289.3° C. (dec); $^1$H-NMR (DMSO-$d_6$, 400 MHz) δ 1.49-1.55 (m, 4H, cyclopentyl H), 1.61-1.68 (m, 2H, cyclopentyl H), 1.83-1.87 (m, 2H, cyclopentyl H), 2.29 (s, 3H, $CH_3$), 3.42 (s, 3H, $NCH_3$), 4.14-4.18 (m, 1H, CH), 6.12 (s, 1H), 8.71-8.73 (d, J=7.05 Hz, 1H, NH); MS (m/z) 251 ($M^+$+1), 166.

1-Cyclopropyl-3-hydroxy-6-methyl-4-oxo-1,4-dihydro-pyridine-2-carboxylic Acid Cyclopropylamide [Apo6618]

M.p. 241-143° C.; $^1$H-NMR (DMSO-$d_6$, 400 MHz) δ 0.53 (m, 2H, cyclopropyl-H), 0.71 (m, 2H, cyclopropyl-H), 0.94-1.00 (m, 4H, cyclopropyl-H), 2.42 (s, 3H, $CH_3$), 2.79 (m, 1H, CH), 3.30 (m, 1H, CH), 6.08 (s, 1H, CH), 8.54 (br, s, 1H, NH); MS (m/z) 249 ($M^+$+1).

Example 7

Preparation of 3-benzyloxy-1-cyclopropyl-6-methyl-oxo-1,4-dihydro-pyridine-2-carboxylic Acid To a suspension of 3-(benzyloxy)-6-methyl-4-oxo-4H-pyran-2-carboxylic acid (70 g, 0.27 mol) in MeOH (350 mL) in a 3-necked RBF (round bottom flask) fitted with a mechanical stirrer was added cyclopropylamine (120 mL, 1.72 mol). A clear light yellow solution resulted. The reaction mixture was refluxed for ca. 19 h. Volatiles were removed in vacuo and the residue was dissolved in water (700 mL) with stirring. The aqueous mixture was filtered through a pad of Celite®. The filtrate was placed in a 3-necked RBF fitted with a mechanical stirrer, and cooled in an ice bath. Conc. HCl was added until the pH was ca. 1-2, and voluminous "orange" solid precipitated out. Acetone (200 mL) was added to the suspension. The solid was then collected by suction filtration, thoroughly washed with acetone, and air-dried. The title compound was obtained as an off-white solid (71.0 g, 88%). Mp: 139.0-139.5° C.; $^1$H-NMR (300 MHz, DMSO-D$_6$) δ (ppm): 0.98-1.15 (m, 4H, 2 c-CH$_2$), [2.37 (s)+2.40 (s), rotamers, 3/2 ratio, 3H, CH$_3$)], 3.30-3.50 (m, 1H, c-CH), 5.00-5.05 (m, 2H, CH$_2$Ph), 6.20-6.25 (m, 1H, C=CH), 7.28-7.50 (m, 5H, Ph); MS (m/z): 300.2 (M$^+$+1), 256.2, 192.2, 164.4, 91.0 (100%); Anal. Calcd. for C$_{17}$H$_{17}$NO$_4$: C, 68.21; H, 5.72; N, 4.68%. Found: C, 67.76; H, 5.76; N, 4.61%.

Example 8

Synthesis of 3-benzyloxy-1-cyclopropyl-6-methyl-4-oxo-1,4-dihydro-pyridine-2-carboxylic Acid Methylamide To a cold suspension (ice-salt bath, internal temp=−5° C.) of 3-benzyloxy-1-cyclopropyl-6-methyl-oxo-1,4-dihydropyridine-2-carboxylic acid (30 g, 0.10 mol), CH$_2$Cl$_2$ (150 mL) and DMF (7.8 mL, 0.10 mol) in a 3N-RBF (round bottom flask) fitted with a mechanical stirrer was added thionyl chloride (9.5 mL, 0.13 mol) dropwise over a period of 5 minutes. After addition of thionyl chloride, the reaction mixture was still a suspension. The ice-salt bath was removed. The reaction mixture was allowed to warm up to room temperature. Aliquots were removed and quenched with a 2M methylamine solution in THF. The resulting mixture was then analyzed by HPLC. Thus, HPLC monitoring indicated about 96% consumption of starting material after the reaction mixture was stirred at room temperature for 3 h (HPLC, mobile phase: 0.035% HClO$_4$/CH$_3$CN, 80/20, column: symmetry C18 WAT046980, flow rate: 1 ml/min, monitoring wavelength: 260 nm, RT of 3-benzyloxy-1-cyclopropyl-6-methyl-oxo-1,4-dihydro-pyridine-2-carboxylic acid=2.46 min, RT of 3-benzyloxy-1-cyclopropyl-6-methyl-4-oxo-1,4-dihydropyridine-2-carboxylic acid methylamide=5.40 min).

In another 1-L 3N-RBF fitted with a mechanical stirrer was placed dichloromethane (240 mL) and triethylamine (36 mL, 0.26 mol) (ice-salt bath, internal temp=−10° C.). 2M methylamine in tetrahydrofuran (73 mL, 0.146 mol) was added to the cold solution. The acid chloride generated in situ above was transferred to an addition funnel, and slowly added to the amine solution over a period of 30 minutes. An exothermic reaction was noticed, but the internal T was kept at below −5° C. The reaction was completed after 10 min as indicated by TLC (CH$_2$Cl$_2$/MeOH, 9/1 ratio, v/v). The reaction mixture was quenched with water (100 mL), and the mixture was stirred for 5 min. The organic fraction was collected and washed twice more with water, followed by washing with diluted NaOH solution (0.05 M, 3×100 mL), dried over sodium sulfate, filtered and concentrated in vacuo to afford a brown solid. The solid was suspended in 150 mL of a mixture of ethanol and ethyl acetate (2/8 ratio, v/v), and the slurry was stirred for 2 h. The solid was collected by suction filtration, washed with ethyl acetate (50 mL), and was then air-dried. The title compound was thus obtained as a light-pink, slightly brownish solid (14 g, 45%). The material was further purified by column chromatography (5% MeOH:CH$_2$Cl$_2$). M.p. 132-135° C.; $^1$H-NMR (CDCl$_3$, 400 MHz) δ 1.05 (m, 4H, cyclopropyl-H), 2.38 (s, 3H, CH$_3$), 2.70 (d, J=1.8 Hz, 3H, NCH$_3$), 3.35 (m, 1H, CH), 5.07 (s, 2H, CH$_2$), 6.14 (s, 1H, CH), 7.15 (br, 1H), 7.35 (m, 5H, ArH); $^{13}$C (CDCl$_3$) δ 9.48, 20.30, 25.86, 34.15, 74.01, 118.16, 127.79, 128.06 (2C), 128.22 (2C), 137.35, 142.05, 143.98, 149.91, 162.01, 173.89; MS (m/z): 313 (M$^+$+1).

In a similar manner, the following compounds were prepared:

3-(Benzyloxy)-N-(cyclohexylmethyl)-1-cyclopropyl-6-methyl-4-oxo-1,4-dihydropyridine-2-carboxamide $^1$H-NMR (CD$_3$OD, 400 MHz) δ 0.90-0.96 (m, 3H), 1.13-1.23 (m, 3H), 1.45-1.54 (m, 1H), 1.64 (br.m, 4H), 1.73-1.76 (br.m, 4H), 2.56 (s, 3H, CH$_3$), 3.12-3.13 (d, J=6.8 Hz, 2H), 3.36-3.40 (m, 1H, CH), 5.09 (s, 2H), 6.43 (s, 1H), 7.31-7.37 (m, 3H), 7.43-7.45 (m, 2H); MS (m/z): 395 (M$^+$+1).

3-(Benzyloxy)-1-cyclopropyl-6-methyl-2-(morpholin-4-ylcarbonyl)pyridin-4(1H)-one $^1$H-NMR (CDCl$_3$, 400 MHz) δ 0.87-0.94 (br.m, 1H), 1.09-1.13 (m, 1H), 1.25-1.30 (m, 2H), 2.56 (s, 3H, CH$_3$), 3.30-3.42 (m, 2H), 3.45-3.69 (m, 6H), 3.84-3.90 (m, 1H, CH), 4.74-4.77 (d, J=10.4 Hz, 1H), 5.54-5.56 (d, J=10.6 Hz, 1H), 6.80 (br.s, 1H, NH), 7.36-7.41 (m, 5H, ArH); MS (m/z): 369 (M$^+$+1).

3-(Benzyloxy)-1-cyclopropyl-6-methyl-N-(3-methylbutyl)-4-oxo-1,4-dihydropyridine-2-carboxamide $^1$H-NMR (CDCl$_3$, 400 MHz) δ 0.86-0.88 (d, J=6.4 Hz, 6H, 2CH$_3$), 1.04-1.09 (m, 4H), 1.27-1.37 (m, 2H), 1.55-1.60 (m, 1H, CH), 2.37 (s, 3H, CH$_3$), 3.20-3.25 (m, 2H, CH$_2$), 3.34-3.37 (m, 1H, CH), 5.09 (s, 2H, CH$_2$), 6.10 (s, 1H), 7.30-7.38 (m, 5H, ArH), 7.23-2.28 (br.t, 1H, NH).

3-(Benzyloxy)-N-cyclohexyl-1-cyclopropyl-6-methyl-4-oxo-1,4-dihydropyridine-2-carboxamide $^1$H-NMR (CDCl$_3$, 400 MHz) δ 1.15-1.30 (m, 3H), 1.31 (br.m, 1H), 1.34 (br.m, 5H), 1.66-1.70 (m, 1H), 2.78 (s, 3H, CH$_3$), 3.30-3.34 (m, 1H), 3.42-3.51 (m, 2H), 3.67-3.69 (m, 1H), 3.80-3.83 (m, 1H), 4.82-4.85 (d, J=10.3 Hz, 1H), 5.37-5.40 (d, J=10.5 Hz, 1H), 7.34 (br.m, 5H, ArH), 7.86 (s, 1H).

3-(Benzyloxy)-1-cyclopropyl-N-hexyl-6-methyl-4-oxo-1,4-dihydropyridine-2-carboxamide $^1$H-NMR (CDCl$_3$, 400 MHz) δ 0.89-0.92 (t, J=6.6 Hz, 3H, CH$_3$), 1.25-1.32 (m, 6H), 1.40-1.47 (m, 4H), 1.64-1.70 (m, 2H, CH$_2$), 2.54 (s, 3H, CH$_3$), 3.43-3.48 (m, 2H, CH$_2$), 3.91-3.93 (m, 1H, CH), 5.10 (s, 2H, CH$_2$), 7.37-7.46 (m, 6H, ArH and C=CH), 9.24 (br.t, 1H, NH); MS (m/z): 383 (M$^+$+1).

3-(Benzyloxy)-1-cyclopropyl-6-methyl-2-[(4-methylpiperazin-1-yl)carbonyl]pyridin-4(1H)-one $^1$H-NMR (CDCl$_3$, 400 MHz) δ 0.85-0.88 (m, 1H), 1.06-1.29 (m, 4H), 1.40-1.45 (br.m, 2H), 1.50-1.58 (br.m, 4H), 2.51 (s, 3H, CH$_3$), 3.12-3.17 (m, 1H), 3.35-3.48 (m, 3H), 3.75-3.78 (m, 1H, CH), 4.76-4.78 (d, J=10.6 Hz, 1H), 5.53-5.56 (d, J=10.7 Hz, 1H), 6.68 (br.s, 1H, NH), 7.30-7.43 (m, 5H, ArH); MS (m/z): 382 (M$^+$+1).

3-(Benzyloxy)-1-cyclopropyl-N,N,6-trimethyl-4-oxo-1,4-dihydropyridine-2-carboxamide $^1$H-NMR (CDCl$_3$, 400 MHz) δ 1.16-1.20 (m, 2H), 1.27-1.33 (m, 1H), 1.87-1.95 (m, 1H), 2.78 (s, 3H, CH$_3$), 3.05 (s, 3H, CH$_3$), 3.08 (s, 3H, CH$_3$), 3.62-3.68 (m, 1H, CH), 4.86-4.90 (d, J=10.8 Hz, 1H), 5.33-5.38 (d, J=10.8 Hz, 1H), 7.29-7.33 (m, 5H, ArH), 7.77 (s, 1H, NH); MS (m/z): 327 (M$^+$+1).

Example 9

A. Preparation of 1-cyclopropyl-3-hydroxy-6-methyl-4-oxo-1,4-dihydro-pyridine-2-carboxylic Acid Methylamide Step a. Synthesis of 1-cyclopropyl-3-hydroxy-6-methyl-4-oxo-1,4-dihydro-pyridine-2-carboxylic Acid Methylamide To a suspension of 3-benzyloxy-1-cyclopropyl-6-methyl-4-oxo-1,4-dihydro-pyridine-2-carboxylic acid methylamide (10.0 g, 0.032 mol) in methanol (40 mL) and water (2.6 mL) at ice-bath temperature, was added conc. HCl (3.9 mL) dropwise. The resulting clear brown solution was stirred at room temperature for ca. 5 min, then nitrogen gas was bubbled into the solution for ca. 5 min. Pd—C (10% wet, 5% w/w, 0.5 g) was added and the reaction vessel was purged with hydrogen twice. The mixture was hydrogenated in a Parr reactor under 50 psi hydrogen pressure at RT, and the progress of the reaction was monitored by HPLC over 3 h. The reaction was over after 3 h.

Excess hydrogen was evacuated and nitrogen gas was bubbled into the solution for about 5 min. The reaction mixture was filtered over pre-treated Celite® (previously washed with a 0.1N standard solution of 1-cyclopropyl-3-hydroxy-6-methyl-4-oxo-1,4-dihydro-pyridine-2-carboxylic acid methylamide in methanol), and the cake was washed with 6×10 mL of methanol. The volume of the filtrate was reduced to about 30 mL under reduced pressure. The residue was cooled in ice and some solid started to precipitate out. A 2N NaOH solution (25 mL) was added until the pH was about 5, and the mixture was stirred for about 10 min. Methyl tert-butyl ether (MTBE, 30 mL) was added, and the resulting mixture was stirred at ice-bath temperature for 30 min. The solid was collected by suction filtration, twice thoroughly washed with a mixture of 5 mL of EtOH/MTBE (1/2 ratio). HPLC condition for reaction monitoring using Hewlett Packard series 1100 HPLC: symmetry C18 column (WAT046980), gradient 0.035% HClO$_4$/CH$_3$CN, min-% CH$_3$CN: 0-10; 6-10; 7-20 and 15-20, λ at 210, 260 and 285 nm; retention time of 1-cyclopropyl-3-hydroxy-6-methyl-4-oxo-1,4-dihydro-pyridine-2-carboxylic acid methylamide is 2.099 min.

Step b. Purification of 1-cyclopropyl-3-hydroxy-6-methyl-4-oxo-1,4-dihydro-pyridine-2-carboxylic Acid Methylamide The suspension of crude product obtained as described in Step a in a 1/1 mixture of EtOH/distilled water (14 mL total) was stirred at ice-bath temperature for 1 h. The solid was collected by suction filtration, and washed 2× thoroughly with 5 mL of a 1/1 mixture of pre-cooled EtOH/distilled water. The title compound, a light pinkish solid, was dried to constant weight at 40° C. under vacuum for 16 h. This product gave a negative silver nitrate test, and weighed 5.3 g (74% total yield, steps a and b).

$^1$H-NMR (300 MHz, DMSO-D$_6$) δ (ppm): 0.94-0.99 (m, 4H, 2 c-CH$_2$), 2.39 (s, 3H, CCH$_3$), 2.76 (d, J=4.4 Hz, 3H, NHCH$_3$), 3.28-3.31 (m, 1H, c-CH), 6.08 (s, 1H, C=CH), 8.44 (br. q., 1H, NHCH$_3$); $^{13}$C-NMR (75 MHz, DMSO-D$_6$) δ (ppm): 9.1, 19.9, 25.8, 33.7, 112.3, 130.1, 143.3, 148.7, 161.8, 170.6; MS/MS (+ve ES): MS (m/z) 223 (M$^+$+1), 192.1, 164.2 (M$^+$-CONHCH$_3$, 100%), 150.1, 136.3; Elemental Analysis: Anal. Calcd. for C$_{11}$H$_{14}$N$_2$O$_3$: C, 59.45; H, 6.35; N, 12.60%. Found: C, 59.19; H, 6.07; N, 12.53%; IR (KBr) cm$^{-1}$: 3300 (NH), 1670, 1653, 1495 (C=C).

B. Preparation of N-(Cyclohexylmethyl)-1-cyclopropyl-3-hydroxy-6-methyl-4-oxo-1,4-dihydropyridine-2-carboxamide

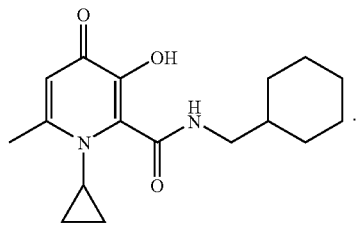

A mixture of 3-(benzyloxy)-N-(cyclohexylmethyl)-1-cyclopropyl-6-methyl-4-oxo-1,4-dihydropyridine-2-carboxamide (2.0 g, 4.8 mmol), Pd/C (10% wet, 0.45 g) in ethanol (150 mL) was hydrogenated in a Parr apparatus at 50 psi of hydrogen pressure for 16 h. The reaction mixture was filtered over a pad of Celite® and the Celite® was thoroughly washed with EtOH (25 mL). Evaporation of the solvent afforded a pale pink solid. The solid was dissolved in hot methanol, then cooled to RT as solid product precipitated out. The solid was collected by suction filtration. The mother liquor was concentrated in vacuo and the residual solid was again dissolved in hot methanol and cooled to RT to precipitate out the product, which was then collected. This process was repeated one more time. The three combined white solid fractions weighed 0.95 g (63% yield).

$^1$H-NMR (CDCl$_3$, 400 MHz) δ 0.84-0.88 (m, 2H, CH$_2$ of c-Pr), 1.03-1.09 (m, 2H, CH$_2$ of c-Pr)), 1.06-1.31 (m, 5H), 1.65-1.87 (m, 6H), 2.50 (s, 3H, CH$_3$), 3.33-3.36 (m, 2H, CH$_2$N), 3.51 (s, 1H), 3.58-3.61 (m, 1H, CH of c-Pr), 6.27 (s, 1H, C=CH), 6.80 (br.t, 1H, NH); MS (m/z): 305 (M$^+$+1).

C. The Following Compounds were Prepared in a Similar Fashion

1-Cyclopropyl-3-hydroxy-6-methyl-N-(3-methylbutyl)-4-oxo-1,4-dihydropyridine-2-carboxamide

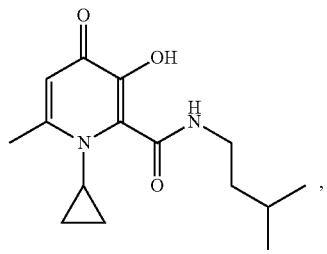

Yield: 88%; $^1$H-NMR (CDCl$_3$, 400 MHz) δ 0.85-0.89 (m, 1H), 0.98-1.00 (d, J=6.4 Hz, 6H, 2CH$_3$), 1.15-1.19 (m, 2H), 1.54-1.60 (m, 2H), 1.72-1.77 (m, 1H, CH), 2.50 (s, 3H, CH$_3$), 3.49-3.53 (m, 2H, CH$_2$), 3.57-3.60 (m, 1H, CH), 3.72 (br.s, 1H), 6.27 (s, 1H), 7.23 (br.t, 1H, NH); MS (m/z): 279 (M$^+$+1).

1-Cyclopropyl-N-hexyl-3-hydroxy-6-methyl-4-oxo-1,4-dihydropyridine-2-carboxamide

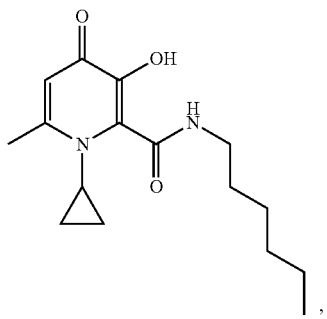

Yield: 87%; $^1$H-NMR (CDCl$_3$, 400 MHz) δ 0.90-0.94 (t, J=6.8 Hz, 3H, CH$_3$), 1.27-1.47 (m, 10H), 1.68-1.73 (m, 2H), 2.70 (s, 3H, CH$_3$), 3.47-3.52 (m, 2H, CH$_2$), 3.85-3.88 (m, 1H, CH), 7.05 (s, 1H, C=CH), 8.30 (br.t, 1H, NH); MS (m/z): 293 (M$^+$+1).

N-Cyclohexyl-1-cyclopropyl-3-hydroxy-6-methyl-4-oxo-1,4-dihydropyridine-2-carboxamide

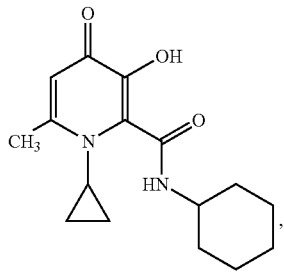

Yield: 91%; $^1$H-NMR (CDCl$_3$, 400 MHz) δ 0.98-1.05 (m, 1H), 1.21-1.38 (m, 3H), 1.60-1.80 (br.m, 7H), 2.71 (s, 3H, CH$_3$), 3.32-3.37 (m, 1H), 3.46-3.50 (m, 1H), 3.55-3.64 (m, 2H), 3.92-3.99 (m, 1H), 6.88 (s, 1H, C=CH); MS (m/z): 277 (M$^+$+1).

1-Cyclopropyl-3-hydroxy-N,N,6-trimethyl-4-oxo-1,4-dihydropyridine-2-carboxamide

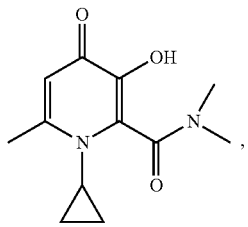

Yield: 97%; $^1$H-NMR (CD$_3$OD 300 MHz) δ 0.98-1.10 (m, 1H), 1.15-1.43 (m, 3H), 2.76 (s, 3H, CH$_3$), 3.07 (s, 3H, CH$_3$), 3.16 (s, 3H, CH$_3$), 3.70-3.76 (m, 1H, CH), 7.10 (s, 1H, C=CH); $^{13}$C-NMR (CD$_3$OD, 75 MHz) δ 9.5, 10.9, 21.3, 35.0, 38.1, 38.8, 114.4, 138.8, 142.9, 154.7, 162.5, 162.8; MS (m/z): 237 (M$^+$+1).

1-Cyclopropyl-3-hydroxy-6-methyl-2-[(4-methylpiperazin-1-yl)carbonyl]pyridin-4(1H)-one

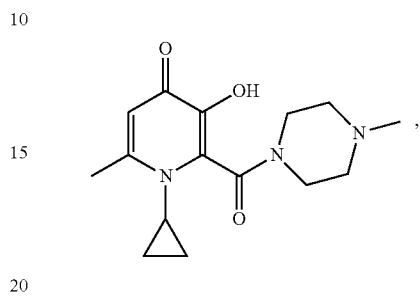

Yield: 96%; $^1$H-NMR (CD$_3$OD, 300 MHz) δ 0.89-1.00 (m, 1H), 1.06-1.29 (m, 3H), 1.52-1.85 (br.m, 8H), 2.56 (s, 3H, CH$_3$), 3.40-3.60 (m, 3H), 3.88-3.98 (m, 1H, CH), 6.48 (s, 1H, C=CH); $^{13}$C-NMR (CD$_3$OD 75 MHz) δ 10.0, 11.0, 21.0, 25.4, 26.4, 27.0, 36.5, 43.8, 49.2, 114.7, 132.9, 144.5, 152.8, 162.4, 170.2.

N,1-Dicyclopropyl-3-hydroxy-6-methyl-4-oxo-1,4-dihydropyridine-2-carboxamide

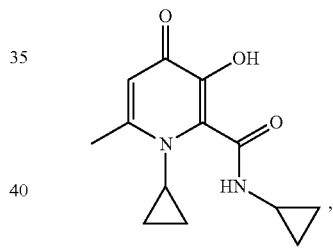

$^1$H-NMR (CDCl$_3$, 400 MHz) δ 0.68-0.70 (m, 2H), 0.85-0.95 (m, 4H), 1.15-1.26 (m, 2H), 2.70 (s, 3H, CH$_3$), 2.91-2.98 (m, 1H), 3.50-3.61 (m, 1H), 6.26 (s, 1H, C=CH), 7.10 (br.s, 1H, NH); MS (m/z): 249 (M$^+$+1).

1-Cyclopropyl-3-hydroxy-6-methyl-2-(morpholin-4-ylcarbonyl)pyridin-4(1H)-one

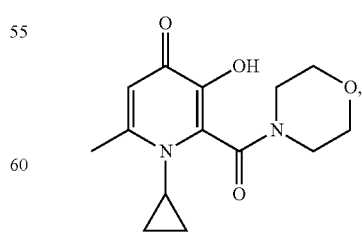

$^1$H-NMR (CD$_3$OD, 300 MHz) δ 1.00-1.10 (m, 1H), 1.20-1.45 (m, 3H), 2.73 (s, 3H, CH$_3$), 3.45-3.53 (m, 2H), 3.62-3.86 (m, 6H), 3.90-4.00 (m, 1H), 7.02 (s, 1H, C=CH); $^{13}$C-NMR (CD$_3$OD, 75 MHz) δ 10.3, 11.1, 21.3, 38.6, 43.6, 48.3, 67.4, 67.7, 114.5, 137.2, 143.3, 154.7, 161.2, 163.7; MS (m/z): 279 (M$^+$+1).

Example 10 pka Determination for Apo6619 by Potentiometric Titration

The pKa values of ligands were determined by potentiometric titration when a ligand concentration greater than $1 \times 10^{-2}$ M in water could be prepared. In a typical experiment, the sample solution ($2.67 \times 10^{-2}$ M) was prepared by the following method: Apo6619 (92.6 mg) was weighed into a 25-ml beaker, followed by the addition of 0.1 M NaCl (15 ml). The mixture was sonicated for 10 minutes to give a clear colorless solution. Nitrogen gas was then allowed to bubble through the solution. 1.000 N Hydrochloric acid (624 µl, 1.5 equivalent) was added to the solution to give pH 1.88. The solution was allowed to equilibrate at 22° C. for 60 minutes.

The solution was then titrated against 1.000 N NaOH at 22° C. to reach pH 11.8. For each addition of base, the solution was allowed to equilibrate until a constant pH reading was reached. The volume of the base added and the pH reading were recorded for each measurement. 137 measurements were taken to finish the experiment.

The data set of pH vs. base volume was analyzed using Hyperquad 2000 (Version 2.1, Peter Gans, University of Leeds). Given the model: L$^-$+H$^+$↔LH (pka$_1$) and LH+ H$^+$↔LH$_2^+$ (pKa$_2$), the pKa values of Apo6619 were optimized as pka$_1$=8.6 and pKa$_2$=2.5.

Example 11 pKa Determination for Apo6617 by Spectrophotometric Titration

The pKa values of ligands can be determined by spectrophotometric titration when both the conjugated acid and base absorb in the UV-Visible region. In a typical experiment, the sample solution was prepared by the following method: Apo6617 (0.792 mg) was weighed into an 80-ml beaker, followed by the addition of 0.1 M NaCl (50 ml). The mixture was sonicated for 5 minutes to give a clear colorless solution. Nitrogen gas was allowed to bubble through the solution. 1.000 N NaOH (50 µl) was added to give pH 10.9. The solution was allowed to equilibrate at 22° C. for 1 hour. A sipper system was used for the circulation of the sample solution between the beaker and the flow cell.

The sample solution was titrated against standard hydrochloric acid solutions at 22° C. to reach pH 1.40. After each addition of acid the solution was allowed to equilibrate until a constant pH reading was reached. The pH and the UV-Vis spectrum were recorded for each measurement. The peak wavelengths of the deprotonated species (L$^-$), the neutral species (LH), and the protonated species (LH$_2^+$) were 314 nm, 281 nm, and 249 nm, respectively. In the region of pH>6, after each addition of acid there was a slight decrease in the absorbance at 314 nm and a slight increase at 281 nm in each spectrum, whereas in the region of pH<5, after each addition of acid there was a slight decrease in the absorbance at 281 nm and a slight increase at 249 nm in each spectrum. The solution was titrated until there was no obvious change in the spectra after several subsequent additions of acid. 116 measurements were taken to finish the experiment.

The resulting data set was then analyzed using pHAB (Peter Gans, University of Leeds). The pKa values of Apo6617 were optimized as pka$_1$=8.6 and pKa$_2$=2.5.

Example 12

Stoichiometry of Fe-Apo6622 Complexes by Job's Method

In a typical experiment, Fe-Apo6622 complex solutions were prepared by mixing a stock solution of Fe$^{3+}$ (atomic absorption standard, 1005 µg/ml in 1 wt. % HCl, Aldrich) and a stock solution of Apo6622 ($6.98 \times 10^{-3}$ M in 0.1 M MOPS pH 7.4). 12 sample solutions were prepared. While the sum of the total iron concentration ($C_{total}^{iron}$) and the total ligand concentration ($C_{total}^{L}$) in each of the 12 sample solutions was kept constant ($8.00 \times 10^{-4}$ M), the molar fraction of the ligand, α ($\alpha = C_{total}^{L}/(C_{total}^{L}+C_{total}^{iron})$), for the 12 sample solutions were different and were prepared as 0, 0.1, 0.2, 0.3, 0.4, 0.5, 0.6, 0.7, 0.75, 0.8, 0.9, and 1.0, respectively. The total volume for each of the 12 sample solutions was 5 ml, using MOPS (0.1 M, pH 7.4) as the solvent. The pH of the 12 solutions was adjusted by adding NaOH to pH 7.4. The sample solutions were vortexed at room temperature for 3 hours, and then placed in a Dubnoff Metabolic Shaking Incubator at 25° C. and at 90 RPM overnight. The sample solutions were centrifuged at 4000 rpm for 15 minutes, and then placed back in the incubator at 25° C. without shaking. The UV-Vis spectrum was recorded at 25° C. for each of the 12 solutions.

A Job's plot was created with the absorbance at 450 nm as the y-axis and α as the x-axis. A maximum absorbance was found at α=0.75, which corresponds to an iron:ligand ratio of 1:3 in the complexes. The Job's plot result is shown in FIG. (1).

Proceeding in a similar manner, the Job's plots of Fe-Apo6617 and Fe-Apo6619 were created. They are shown in FIGS. (2) and (3).

Example 13

Distribution Coefficient Determination

MOPS buffer (50 mM, pH=7.4) and 1-octanol were used as the aqueous phase and the organic phase, respectively, for distribution coefficient determinations. The MOPS buffer and 1-octanol were pre-saturated with each other before use.

In a typical experiment, an organic stock solution of Apo6618 (1-cyclopropyl-3-hydroxy-6-methyl-4-oxo-1,4-dihydro-pyridine-2-carboxylic acid cyclopropylamide) was prepared by weighing out 0.50 mg of the compound into a 10-mL volumetric flask and bringing to volume with 1-octanol. The solution was then sonicated for 60 minutes so that the sample could dissolve completely. The concentration of the stock solution was calculated as $C^0_{org}=2.0 \times 10^{-4}$ M. The organic standard solution of Apo6618 with $2.0 \times 10^{-5}$ M was prepared in a 10-mL volumetric flask by 10 times dilution of the stock solution with 1-octanol. The sample solution was prepared in a 10-mL volumetric flask. The stock sample solution (3 ml) was pipetted into the flask followed by the addition of MOPS buffer (3 ml). The standard and sample solutions were then vortexed for 2 hours. After vortexing, the solutions were transferred to test tubes and centrifuged at 4000 rpm for 15 minutes. UV-Vis spectra were recorded for the standard solution and the organic (top) phase of the sample solution at 22° C. The distribution coefficient, $D_{7.4}$, was calculated using the following equation:

$$D_{7.4}=[A_{org}/(C^0_{org}\epsilon_{org}-A_{org})] \times (V_{aqu}/V_{org})$$

Where $\epsilon_{org}$=the molar extinction coefficient of the peak wavelength ($\lambda_{max}$) obtained from the UV-Vis spectrum of the organic standard solution; $A_{org}$=absorbance of the organic phase in the sample solution at the same $\lambda_{max}$; $C^0_{org}$=the concentration of the stock solution; $V_{aqu}$=the volume of MOPS buffer in the sample solution; $V_{org}$=the volume of the stock solution in the sample solution.

Example 14

Determination of Metal Complexation Constants

A. Instrumental and Chemicals.

A pH meter (Accumet Research AR15, 13-636-AR15, Fisher) and a combination electrode (Accumet Standard-size Glass Combination Electrode, 13-620-285, Fisher) were used for pH measurements. Before using, the electrode was calibrated with three standard buffer solutions (pH 4.00, pH 7.00, and pH 10.00, Fisher). The titrant was added manually by using digital pipettes (Eppendorf). An UV-visible spectrophotometer (Agilent 8453) was used for UV-Vis absorbance measurements.

A sipper system (89068D Agilent) was used whenever pH-dependent absorbencies were measured. A vortexer (VX-2500 Multi-tube Vortexer, VWR Scientific Products) was used for the preparation of sample solutions in both distribution coefficient and Job's plot experiments.

The metal stock solutions were purchased from Aldrich: Iron atomic absorption standard solution (1000 μg/ml of Fe in 1 wt. % HCl); Aluminum atomic absorption standard solution (1000 μg/ml of Al in 1 wt. % HCl); Calcium atomic absorption standard solution (1000 μg/ml of Ca in 1 wt. % HCl); Copper atomic absorption standard solution (1000 μg/ml of Cu in 1 wt. % $HNO_3$); Magnesium atomic absorption standard solution (1000 μg/ml of Mg in 1 wt. % $HNO_3$); Manganese atomic absorption standard solution (1000 μg/ml of Mn in 1 wt. % $HNO_3$); Zinc atomic absorption standard solution (1000 μg/ml of Zn in 1 wt. % HCl). The standard Sodium Hydroxide and Hydrochloric acid solutions were purchased from VWR Scientific Products. MOPS (3-[N-Morpholino] propanesulfonic acid) was purchased from Sigma-Aldrich.

B. Determination of Stepwise Formation Constants for Fe-Apo6619 System by Spectrophotometric Titration. Apo6619 is 1-cyclopropyl-3-hydroxy-6-methyl-4-oxo-1,4-dihydro-pyridine-2-carboxylic Acid Methylamide.

Stepwise formation constants for $M^{n+}$-ligand systems were determined by spectrophotometric titration when metal complexes have a strong absorbance in the visible region due to ligand to metal charge transfer. In a typical experiment, the sample solution was prepared according to the following method: Apo6619 (10.7 mg) was weighed into an 80-ml beaker, followed by the addition of 0.1 M NaCl (50 ml). The mixture was sonicated for 10 minutes to give a clear colorless solution. Iron stock solution (atomic absorption standard, Aldrich, 496 μl, 8.93E-06 moles) was pipetted into the solution followed by the addition of 1.000 N NaOH (137 μl). The molar ratio between the total iron and the total Apo6619 was 1:5.4. The mixture was allowed to equilibrate at room temperature overnight. Nitrogen was allowed to bubble through the solution. 1.000 N Hydrochloric acid (3 ml) was then added to the solution to give pH 1.5. The solution was allowed to equilibrate at 22° C. for 3 hours.

A sipper system was used for the circulation of the sample solution between the beaker and the flow cell.

The sample solution was titrated against standard NaOH solutions at 22° C. to reach pH 6.89. After each addition of base the solution was allowed to equilibrate until a constant pH reading was reached. The pH and the UV-Vis spectrum were recorded for each measurement. For each measurement enough base was added so that there was a slight increase in the absorbance of the spectrum. The solution was titrated until there was no obvious increase in the spectra after several subsequent additions of base. Altogether 64 measurements were taken to finish the experiment.

The resulting data set was then analyzed using pHAB. Given the model: $L^-+H^+ \leftrightarrow LH$ ($pKa_1$), $LH+H^+ \leftrightarrow LH_2^+$ ($pKa_2$), $Fe^{3+}+L^- \leftrightarrow FeL^{2+}$ ($K_1$), $FeL^{2+}+L^- \leftrightarrow FeL_2^+$ ($K_2$), $FeL_2^++L^- \leftrightarrow FeL_3$ ($K_3$), and $\beta_3=K_1K_2K_3$, the stepwise formation constants for Fe-Apo6619 system were optimized as log $K_1$=12.5(1); log $K_2$=11.6(1); log $K_3$=9.5(1); log $\beta_3$=33.6(2).

C. Determination of Stepwise Formation Constants for Al-Apo6619 System by Potentiometric Titration.

Stepwise formation constants for $M^{n+}$-ligand system were determined by potentiometric titration when metal complexes ($\geq 0.002$ M) do not precipitate during titration. In a typical experiment, the sample solution was prepared by the following method: Apo6619 (31.91 mg) was weighed into a 25-ml beaker followed by the addition of 0.1 M NaCl (18.9 ml). The mixture was sonicated for 10 minutes to give a clear colorless solution. Aluminum stock solution (atomic absorption standard, Aldrich, 971 μl, $3.59 \times 10^{-5}$ mole) was pipetted into the solution followed by the addition of 1.000 N NaOH (229 μl) to give pH 8.56. The molar ratio between the total Aluminum and the total Apo6619 was 1:4. For $M^{2+}$ metals, a molar ratio of 1:3 was used. Nitrogen was allowed to bubble through the solution. The mixture was allowed to equilibrate at 22° C. for 2 hours. 1.000 N Hydrochloric acid (264 μl) was then added to the solution to give pH 2.20. The solution was allowed to equilibrate at 22° C. for 1 hour.

The solution was titrated against 1.000 N NaOH at 22° C. to reach pH 11.0. For each addition of base, the solution was allowed to equilibrate until a constant pH reading was reached. The volume of the base added and the pH reading were then recorded for each measurement. 93 measurements were used in the experiment.

The data set of pH vs. base volume was analyzed using Hyperquad 2000. Given the model: $L^-+H^+ \leftrightarrow LH$ ($pKa_1$), $LH+H^+ \leftrightarrow LH_2^+$ ($pKa_2$), $Al^{3+}+L^- \leftrightarrow AlL^{2+}$ ($K_1$), $AlL^{2+}+L^- \leftrightarrow AlL_2^+$ ($K_2$), $AlL_2^++L^- \leftrightarrow AlL_3$ ($K_3$), and $\beta_3=K_1K_2K_3$, the stepwise formation constants for Al-Apo6619 system were optimized as log $K_1$=12.6(2); log $K_2$=9.2(1); log $K_3$=8.4(1); log $\beta_3$=30.2(2).

Calculation of $pM^{n+}$ $pM^{n+}$ is defined as $-\log [M(H_2O)_m]^{n+}$ at physiological conditions, i.e.: pH 7.4, a ligand concentration of 10 μM, and a metal concentration of 1 μM.

To calculate $pM^{n+}$ for a $ML_n$ system, $\beta_n$ and pKa values are needed ($\beta_n$ are the formation constants for $M^{n+}+n L^- \leftrightarrow ML_n$; pKa are the equilibrium constants for $L^-+n H^+ \leftrightarrow LH_n^{(n-1)+}$). The $pM^{n+}$ can be calculated by using Hyss software (Hyperquad Stimulation and Speciation software: HYSS2© 2000 Protonic Sofware).

The data obtained from the above determinations for compounds of formula I can be found in Table 1 and 2.

Example 15

Evaluation of Compounds of Formula I in Iron Overloaded Rats

Effectiveness of Apo6619 and Apo6617 in Promoting Urinary and Fecal Iron Excretion in the Iron Overloaded Rat:

The purpose of this study was to determine the effectiveness of Apo6619 and Apo6617 in promoting iron excretion in the iron overloaded rat model. Iron overloading was achieved by administration of iron dextran. Iron overloading using iron dextran has previously been used to assess chelator efficacy in mice (Kontoghiorghes G. J., *Mol. Pharmacol.* 1986, 30(6), 670-3; Bartfay et al., *Cardiovasc Res.* 1999, 43(4), 892-900), gerbils (Hershko et al., *J. Lab Clin Med* 2002, 139, 50-58), rats (Rakba N. *Biochem Pharmacol.* 1998, 55(11):1796-1806) and primates (Bergeron et. al., *Blood,* 1992, 79(7), 1882-1890). The iron loading regime used in this study results in a 20-fold increase in liver iron and a 3.8-fold increase in cardiac iron levels in male rats. Previous studies in this model have demonstrated that this model is not associated with significant abnormalities in animal weight gain, food consumption, clinical chemistry or hematology parameters.

Experimental Protocol:

Six male Sprague-Dawley rats (weighing between 200-250 gms) were received from Charles River Laboratories, Montreal, Quebec, Canada. Rats were iron loaded by administration of iron dextran intraperitoneally at a dose of 100 mg/kg, twice weekly for a period of 4 weeks for a total of 8 injections (iron dextran, Sigma). The total volume of iron dextran injected was 1 mL/kg. Following an eight week period, rats were transferred to metabolic cages (one rat/cage). Once the animals were in the metabolic cages, excreta (both urine and feces) were collected daily for at least 3 day prior to and 4 days following the administration of each chelator. Each of the two chelators (Apo6619 and Apo6617) was administered consecutively. Chelators were administered as a single dose of 450 µmoles/kg by oral gavage at a dose volume of 2-4 mL/kg. The animals were weighed prior to dosing to enable exact dosage administration. Animals were checked daily (eyes, skin and movement) after chelator administration to determine if there were any obvious signs of ill health. Urine and feces were stored at $-20°$ C. until analysis for total iron concentrations.

Animal Diet, Water and Housing:

Rats were housed in a climate and light controlled environment (temperature: $19-25°$ C., relative humidity 40%, 12 hrs light/dark cycle) throughout the study. During the acclimatization, iron loading and equilibration phases, rats were placed in standard cages (2 rats/cage), fed standard rodent chow and given regular tap water ad libitum. Rats were transferred to metabolic cages (one rat/cage, Nalgene, Rochester N.Y.) after iron loading and equilibration. Three days before placement of the rats in the metabolic cages, rats were fed a low iron diet (3 ppm iron, Dyets Inc., Bethlehem, Pa.) and given Millipore water ad libitum. Rats were continued on the low iron diet for the duration of the study. The purpose of placing animals on a low iron diet was to reduce the background noise produced by dietary iron in the fecal samples.

Preparation of Dosing Solution of Chelators:

A 50 mg/ml dosing solution of the chelator of formula I (570 mg) was first dissolved in a mixture of Millipore water (2 ml) and 6N HCl (0.4 ml) and brought up to the final volume (11.4 ml) with Millipore water (9 ml). Final pH of the solutions was adjusted to pH 4 with diluted sodium hydroxide solution. Solutions were protected from light and prepared freshly prior to each administration.

Iron Determinations:

Urine and feces samples were shipped to the Trace Elements Laboratory at the London Health Sciences Center, London, Ontario, Canada for analysis of total iron concentration. Briefly, feces samples were prepared by adding water, heating to $98°$ C., vortexing and subsequently freeze drying. The samples were then mixed, and a representative subsample taken and digested with boiling $HNO_3$ and $H_2O_2$. Feces samples were then diluted 1:100 with ultrapure water prior to running using a high resolution sector field ICP-MS (Finnigan Element 1). Urine samples were digested with 0.1% $HNO_3$ and diluted ⅒ prior to running on the ICP-MS. Appropriate calibration curves using iron spiked samples and NIST traceable standards were used. Samples lying above or below the quantification range were re-run. Since the total amount of urine and feces produced over a given period of time was known as well as rat weight, total iron levels in the urine and feces are expressed as µg/day/kg. Statistical comparisons within and between groups was made using unpaired t-tests. A p value of <0.05 was accepted as significant.

Results:

The rats showed no obvious signs of ill health following administration of any of the chelators. All animals continued to gain weight normally after each of the chelators was administered.

Urinary Excretion:

The effectiveness of Apo6619 and Apo6617 in promoting urinary iron excretion is presented in FIG. 6, below. Baseline urinary excretion, as measured during the 3 days prior to Apo6619 administration was 6±1 pg/day/kg.

This increased to 240±131 µg/day/kg one day after Apo6619 administration (p=0.007). Excretion subsequently declined to 16±5 µg/day/kg the second day after Apo6619 administration, however even these levels were still significantly higher than baseline (p=0.004). By the third day, urinary iron excretion had returned to baseline levels (5±1 µg/day/kg). Apo6617 also resulted in increased iron excretion one and two days after administration (164±55 and 17±13 µg/day/kg, respectively). Although the urinary excretion produced by Apo6619 was numerically greater than that achieved with Apo6617 (240±131 µg/day/kg versus 164±55 µg/day/kg, one day after chelator administration), this difference did not achieve statistical significance due to the fact that one of the six rats exhibited higher urinary excretion with Apo6617 than Apo6619.

For comparative purposes, deferiprone was also studied at a dose of 450 µmoles/kg in the above model but in a different set of rats (n=6). The baseline urinary iron levels measured 9±3 µg/day/kg. These were increased to 80±32 µg/day/kg one day after deferiprone administration (p=0.06) and levels returned to baseline by the second day.

Fecal Excretion:

The effectiveness of Apo6619 and Apo6617 in promoting fecal iron excretion is presented in Table 3. Both the baseline values as well as the post-chelator induced values represent the sum of iron excreted in the three days prior to and following chelator administration, respectively. Both Apo6619 and Apo6617 increased fecal iron excretion at 450 µmoles/kg, but this reached statistical significance only in the Apo6617 group (Apo6619: 4154±1245 µg/day/kg, p=0.08 versus baseline; Apo6617 4411±790 µg/day/kg versus baseline, p=0.008). In a previous study in the same model, deferiprone administered to six rats at a dose of 450 µmoles/kg resulted in fecal iron excretion values of 2157±169 µg/day/kg three days after chelator administration.

Second Rat Study at 113 µMoles/Kg:

A second study was conducted to confirm the efficacy results of Apo6619 and Apo6617 observed in the above study and to further characterize the efficacy of these compounds at doses lower than 450 µmol/kg. The study was conducted in two separate groups of iron overloaded rats. The method of iron overloading, preparation of dosing solutions and assessment of efficacy in these rats was similar to that described in the above study.

The first group of rats (n=6) were treated with Apo6619 consecutively at doses of 28, 113 and 450 µmoles/kg. Similarly, the second group of rats (also n=6) was treated with Apo6617 at these same three doses. A summary of the excretion data is shown in Table 4. Similar to the previous study, both Apo6619 and Apo6617 produced an increase in urinary iron excretion at the 450 µmoles/kg dose (Apo6619: 11±3 at baseline to 335±76 1-day post-Apo6619, p=0.0001; Apo6617: 14±4 at baseline to 183±20 1-day post-Apo6617, p=0.0003). In contrast to the previous study where no significant difference between the urinary efficacy of Apo6619 and Apo6617 was observed at 450 µmoles/kg, in this study it was clear that Apo6619 was more effective than Apo6617 (p=0.004) at this dose. Similarly, at 113 µmol/kg (25 mg/kg), both Apo6619 and Apo6617 increased urinary excretion (p<0.005), but Apo6619 was more effective than Apo6617 (p=0.01). At 28 µmoles/kg, only Apo6617 produced an increase in iron excretion (p=0.01) above baseline. However, the magnitude of the increased excretion was small for both Apo6619 and Apo6617.

Fecal excretion was increased by Apo6619 at 450 µmoles/kg (p=0.03) and there was a trend towards increased excretion with Apo6617 as well (p=0.08). No significant increases in fecal excretion were detectable with either chelator at doses lower than 450 µmoles/kg.

Collectively, both studies show that Apo6619 and Apo6617 result in increased urinary and fecal iron excretion. This excretion is superior to that observed in historical studies with deferiprone in the same model. While Apo6619 produces significantly greater urinary iron excretion as compared to Apo6617 at high doses, the superiority of Apo6619 over Apo6617 in producing increased fecal iron excretion was not evident from these studies. In large part, this is due to both the high, and highly variable "background" levels of iron in the feces (i.e. low signal to noise ratio) making chelator induced increases in iron excretion difficult to detect.

Example 16

A. Preparation of Fe(Apo6617)3 Chelate

A pH 9.7 carbonate buffer was prepared by dissolving 0.84 g of sodium bicarbonate, 1.06 g of sodium carbonate in deionized water and diluting the solution to 50 ml. Apo6617 (1.028 g, 4.62 mmol) was added to the carbonate buffer (25 ml). The heterogeneous mixture was stirred for 15 minutes at room temperature to give a clear solution. Anhydrous ferric chloride (0.2417 g, 1.49 mmol) was added in small portions over 5 min. at room temperature to give a dark red solution. The flask was then sealed with a septum cap and stirred at room temperature for 42 h. Acetonitrile (30 ml) was added and the solvent was evaporated under reduced pressure to give a dry red mass. The solid was dissolved in dichloromethane (90 ml), dried over anhydrous $Na_2SO_4$, filtered and concentrated. The crude product was subjected to purification by flash chromatography using elution gradient (dichloromethane/methanol mixture: 95/5, 90/10, 85/15 and 80/20). A red solid (900 mg) was obtained. The solid was mixed with the mixture of ethyl acetate/methanol (90/10, 60 ml) and stirred at RT for 1 h. The insoluble particulate was filtered and the filtrate evaporate under reduce pressure to give the product (800.5 mg). MS (m/z): 742.6 ($M^+$+Na), 720.4 ($M^+$+1), 634.6, 499.0, 469.6, 360.4, 334.3.

A saturated solution of the Fe(Apo6617)$_3$ was prepared by dissolving 0.2 gm of the material in dichloromethane. The insoluble particulate was filtered. 0.3 ml of ethyl acetate was added to 1 ml of the saturated dichloromethane solution in a vial. The vial was capped at room temperature. The dark brown crystals were removed for crystallography determination. The 3-dimension single crystal structure is shown in FIG. 7. The crystallographic data is shown in Table 5 to 6.

B. Preparation of Fe(Apo6619)$_3$

Apo6619 (4.4488 g, 20.0 mmole) was weighed out into a 100-ml 1-neck round bottom flask equipped with a magnetic stir bar. Deionized water (30 ml) was added to give a suspension. To the mixture was added NaOH solution (3.336 ml of 6.000 N solution, 20.0 mmole) at room temperature to give a clear orange-red solution. $FeCl_3 \cdot 6H_2O$ (1.7735 g, BDH, 97-102%, 6.56 mmole) was weighed out into a 30-ml test tube. Deionized water (4 ml) was added into the test tube. The mixture was vortexed to give a clear yellow solution. The $FeCl_3$ solution was added to the above Apo6619 solution dropwise. The mixture was stirred at room temperature for 6 days. Solid was formed at this time. The solid was collected by suction filtration. The solid was transferred back to the round bottom flask. 50 ml of acetone and 3 ml of deionized water was added. The mixture was stirred for a few hours. The solid was then collected by suction filtration. The solid was air dried to give 3.1 g (yield=66%). MS: 720.6 (M+1). Single crystals of Fe(Apo6619)$_3$ were grown from diffusion of toluene into wet DMF. The X-ray crystal structure of Fe(Apo6619)$_3$ is shown in FIG. 8.

Example 17

Determination of E1/2 of Fe-Apo6619 System

A. Materials & Instruments.

Potassium ferricyanide (III) was purchased from Aldrich. Deferoxamine mesylate (DFO) was purchased from Sigma. Iron atomic absorption standard solution (contains 1005 µg/mL of Fe in 1 wt. % HCl) was purchased from Aldrich. Electrochemical measurements were performed with a cyclic voltammetric analyzer (BAS, CV-50W Potentiostat). Software BAS CV-50W Version 2.31 was used. The following electrodes were used for determining redox potentials of the iron complexes: Ag/AgCl reference electrode (BAS, MF-2052); platinum auxiliary electrode (BAS, MW-1032); and glassy carbon working electrode (BAS, MF-2012). A pH meter (Accumet Research AR15, 13-636-AR15, Fisher Scientific) and pH electrode (AccupHast combination electrode, 13-620-297, Fisher Scientific) were used for pH adjustment of the sample solutions.

B. Preparation of Sample Solutions 2.0 mM solution of Fe(DFO) in 0.1 M NaCl (pH 7.4)

148.1 mg of Deferoxamine mesylate (purity=95%) was accurately weighed out into a 100-mL volumetric flask. The solid was dissolved in about 30 mL of 0.1 M NaCl to give a clear colorless solution. To the solution was added 11.114 mL of the standard iron solution (contains 1005 µg/mL of Fe in 1 wt. % HCl). The solution was diluted with 0.1 M NaCl to the 100 ml mark in the volumetric flask. The resulting solution was vortexed to ensure complete mixing. The solution was transferred to a 200-mL beaker. The pH of the solution was then adjusted to about 7.1 by adding standard solutions of sodium hydroxide. The beaker was then covered with parafilm and the solution was left stirring overnight. The pH of the solution was adjusted to 7.40 in the following test day. The calculated molar ratio between iron$_{total}$ and DFO$_{total}$ is 1:1.07.

2.0 mM solution of Fe(Apo6619)$_3$ in 0.1 M NaCl (pH 7.4)

70.0 mg of Apo6619 was accurately weighed out into a 50-mL volumetric flask. The solid was dissolved in about 15 mL of 0.1 M NaCl to give a clear colorless solution. To the solution was added 5557 µL of the standard iron solution (contains 1005 µg/mL of Fe in 1 wt. % HCl). 0.1 M NaCl was then added to diluted the total volume to 50 ml. The resulting solution was vortexed to ensure complete mixing. The solution was transferred to an 80-mL beaker. The pH of the solution was then adjusted to about 7.1 by adding standard solutions of sodium hydroxide. The beaker was then covered with parafilm and the solution was left stirring overnight. The pH of the solution was adjusted to 7.40 in the following test day. The calculated molar ratio between iron$^{total}$ and Apo6619$_{total}$ is 1:3.15. In a similar manner, a solution of 2.0 mM of Fe(deferiprone)$_3$ in 0.1 M NaCl (pH 7.4) was prepared.

C. Determination of Redox Potentials of Iron Complexes

All potentials in the text are given versus the Ag/AgCl reference electrode. The redox potentials of 2.0 mM of K$_3$Fe(CN)$_6$ in 1.0 M potassium nitrate were measured at the beginning of each working day to verify the proper functioning of the cyclic voltammeter. The redox peak potentials of 2.0 mM solutions of iron complexes at pH 7.4, that is, Fe(DFO), Fe(L1)$_3$, and Fe(Apo6619)$_3$, were determined. The sample solutions of iron complexes were purged with argon for 15 minutes before CV scans, and the solution was under argon during measurements. The glassy carbon working electrode was polished on alumina after each scan. The scan rate used was 300 mV/sec for Potassium ferricyanide (III) solution, and was 450 mV/sec for the solutions of Fe(DFO), Fe(L1)$_3$, and Fe(Apo6619)$_3$. FIG. 9 shows the cyclic voltammograms of iron(III)L$_n$ complexes at pH 7.4: a) K$_3$Fe(CN)$_6$; b) Fe(DFO); c) Fe(L1)$_3$; {L1=deferiprone} and d) Fe(Apo6619)$_3$. The reduction peak potential (E$_p^{red}$), the oxidation peak potential (E$_p^{ox}$), the absolute difference between E$_p^{red}$ and E$_p^{ox}$ ($\Delta E_p$), and redox potential (E$_{1/2}$) of the four iron complexes measured. E$_{1/2}$ value is calculated as (E$_p^{red}$+E$_p^{ox}$)/2 is reported in the table within FIG. 9.

The redox potentials of 2.0 mM of K$_3$Fe(CN)$_6$ in 1.0 M potassium nitrate were measured at the beginning of each working day to verify the proper functioning of the cyclic voltammeter. In a typical measurement, the E$_p^{red}$, E$_p^{ox}$, $\Delta E_p$, and E$_{1/2}$ values of K$_3$Fe(CN)$_6$ determined in this lab using glassy carbon working electrode are 197 mV, 282 mV, 85 mV, and 240 mV, respectively. The values from Bioanalytical Systems Inc. (BAS) using platinum working electrode are 237 mV, 306 mV, 69 mV, and 272 mV, respectively. From a theoretical perspective, $\Delta E_p$ should be about 60 mV for a single electron transfer process. The experimental values are considered in good agreement with those from BAS.

Unlike K$_3$Fe(CN)$_6$, the redox properties of Fe(DFO), Fe(L1)$_3$, and Fe(Apo6619)$_3$ are extremely sensitive to the status of working electrode surface. The redox potentials were reproducible only after careful polishing of the glassy carbon working electrode on alumina after each scan.

The $\Delta E_p$ values of Fe(DFO), Fe(L1)$_3$, and Fe(Apo6619)$_3$ are 112 mV, 107 mV, and 85 mV, respectively. It can be seen clearly (FIG. 9) that the cyclic voltammograms of Fe(DFO), Fe(L1)$_3$, and Fe(Apo6619)$_3$ are basically reversible. Based on these two observations, it is reasonable to assume that the cyclic voltammograms of Fe(DFO), Fe(L1)$_3$, and Fe(Apo6619)$_3$ represent a reversible single electron transfer process for each complex: Fe(III)L$_n$∴Fe(II)L$_n$. The E$_{1/2}$ value of Fe(DFO) determined in this lab is −698 mV versus the Ag/AgCl reference electrode, which is in excellent agreement to literature value (−688 mV) (A. L. Crumbliss et al, *Inorganic Chemistry*, 2003, 42, 42-50). The E$_{1/2}$ value of Fe(Apo6619)$_3$ is −691 mV, which is similar to that of Fe(DFO).

The above examples are provided by way of illustration only and are in no way intended to limit the scope of the invention. One of skill in the art will understand that the invention may be modified in various ways without departing from the spirit or principle of the invention. We claim all such modifications.

The electrochemical properties of iron(III)L$_n$ complexes at pH 7.4 are listed below:

| System | E$_p^{red}$ (mV) | E$_p^{ox}$ (mV) | $\Delta E_p$ (mV) | E$_{1/2}$ (mV) |
|---|---|---|---|---|
| K$_3$Fe(CN)$_6$ | 197 | 282 | 85 | 240 |
| Fe(DFO) | −754 | −642 | 112 | −698 |
| Fe(deferiprone)$_3$ | −887 | −780 | 107 | −834 |
| Fe(Apo6619)$_3$ | −733 | −648 | 85 | −691 |

TABLE 1

Chemical Properties of compounds of formula I.

| Structure | Compound # | D$_{7.4}$ | pKas | Log β$_3$ | pFe$^{3+}$ | QMPR Plus$^{TM}$ software Cal. Human Jejunal Effective Permeability [cm/s × 10$^{−4}$] |
|---|---|---|---|---|---|---|
| 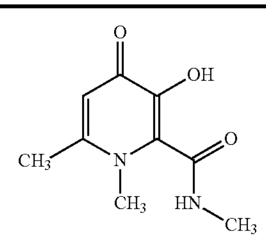 | CP502 | 0.04 | 2.7, 8.5 | 33.6 | 20.9 | 0.81 |

TABLE 1-continued
Chemical Properties of compounds of formula I.
| Structure | Compound # | $D_{7.4}$ | pKas | Log $\beta_3$ | $pFe^{3+}$ | QMPR Plus™ software Cal. Human Jejunal Effective Permeability [cm/s × $10^{-4}$] |
|---|---|---|---|---|---|---|
| 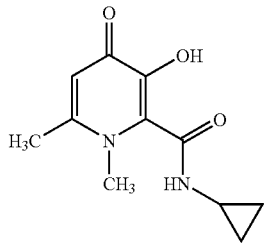 | Apo6617 | 0.099 | 2.4, 8.5 | 33.6 | 20.8 | 1.11 |
| 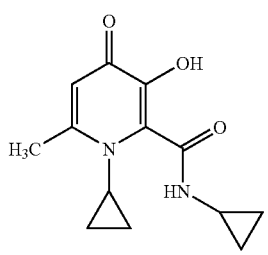 | Apo6618 | 0.331 | 2.5, 8.6 | 33.6 | 20.5 | 1.49 |
| 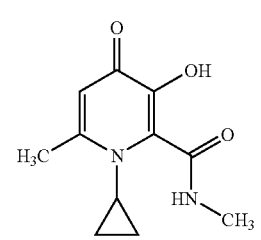 | Apo6619 | 0.109 | 2.5, 8.6 | 33.4 | 20.7 | 1.11 |
| 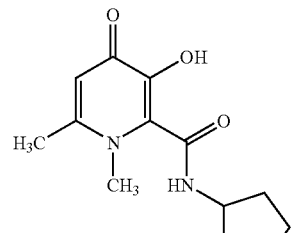 | Apo6620 | 0.78 | 2.7, 8.7 | 33.8 | 20.3 | 1.46 |
| 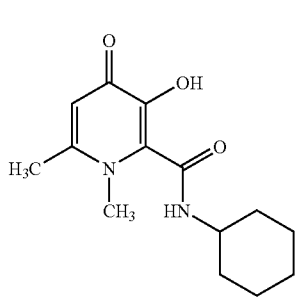 | Apo6621 | 2.2 | 2.5, 8.7 | 34.3 | 20.9 | 1.65 |

TABLE 1-continued

Chemical Properties of compounds of formula I.

| Structure | Compound # | $D_{7.4}$ | pKas | Log $\beta_3$ | pFe$^{3+}$ | QMPR Plus$^{TM}$ software Cal. Human Jejunal Effective Permeability [cm/s × 10$^{-4}$] |
|---|---|---|---|---|---|---|
| 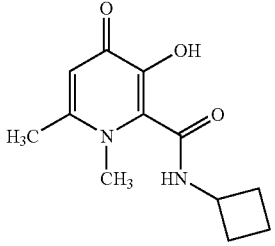 | Apo6622 | 0.357 | 2.8, 8.6 | 33.9 | 20.8 | 1.28 |

TABLE 2

Metal ion binding selectivity of Apo6619 (pKa$_1$ = 2.5, pKa$_2$ = 8.6)

| log scale | Fe(III) | Al(III) | Cu(II) | Zn(II) | Mn(II) | Mg(II) | Ca(II) |
|---|---|---|---|---|---|---|---|
| K$_1$ | 12.5 | 9.3 | 8.9 | 6.3 | 5.1 | 4.1 | 3 |
| K$_2$ | 11.6 | 9.5 | 7.7 | 5.8 | 4.3 | 3.2 | 2.1 |
| K$_3$ | 9.5 | 8.2 | — | — | — | — | — |
| $\beta_2$ | — | — | 16.6 | 12.1 | 9.4 | 7.3 | 5.1 |
| $\beta_3$ | 33.6 | 27 | — | — | — | — | — |
| PM | 20.5 | 13.9 | 10 | 6.4 | 6.0 | 6.0 | 6.0 |

TABLE 3

Effectiveness of Apo6619 and Apo6617 administered at a dose of 450 μmoles/kg in Promoting Fecal Iron Excretion in the Iron Overloaded Rats (n = 6). Values are expressed as μg/day/kg. Fecal excretion values three days after putative chelator administration are given. Values are expressed as mean ± 1SD.

| Test Article | Fecal excretion (μg/daykg) |
|---|---|
| Baseline | 3057 ± 184 |
| Apo6619 | 4154 ± 1245 |
| Apo6617 | 4411 ± 790 |

TABLE 4

Effectiveness of Apo6619 and Apo6617 in Promoting Urinary and Fecal Iron Excretion in the Iron Overloaded Rats (n = 6/group). Values are expressed as μg/day/kg. Fecal excretion values 3 days after chelator administration are given and compared to the baseline values determined 3 days prior to chelator administration. Values are expressed as mean ± 1SD.
Iron excretion data expressed in μg/day/kg (±SD)

| | Compound | | | |
|---|---|---|---|---|
| | Urine (1 day post-chelator) | | Feces (3 days)[1] | |
| Dose Level | Apo6617 | Apo6619 | Apo6617 | Apo6619 |
| 0 (Baseline) | 14 ± 4 | 11 ± 3 | 2300 ± 1003 | 2575 ± 871 |
| 28 μmol/kg | 24 ± 6* | 14 ± 4 | Not Measured | Not Measured |

TABLE 4-continued

Effectiveness of Apo6619 and Apo6617 in Promoting Urinary and Fecal Iron Excretion in the Iron Overloaded Rats (n = 6/group). Values are expressed as μg/day/kg. Fecal excretion values 3 days after chelator administration are given and compared to the baseline values determined 3 days prior to chelator administration. Values are expressed as mean ± 1SD.
Iron excretion data expressed in μg/day/kg (±SD)

| | Compound | | | |
|---|---|---|---|---|
| | Urine (1 day post-chelator) | | Feces (3 days)[1] | |
| Dose Level | Apo6617 | Apo6619 | Apo6617 | Apo6619 |
| 113 μmol/kg | 28 ± 8* | 51 ± 15*τ | 2411 ± 335 | 3033 ± 1076 |
| 450 μmol/kg | 183 ± 20* | 335 ± 76*τ | 3228 ± 437 | 3831 ± 790* |

[1]Assessment of 3-day fecal excretion was required to allow for transit of the iron through the gastrointestinal tract.
*p < 0.05 versus baseline value in the same group
τp < 0.05 versus Apo6617 at the same dose

TABLE 5

Crystal data and structure refinement for Fe(Apo6617)$_3$

| | |
|---|---|
| Identification code | Fe(Apo6617)$_3$ |
| Empirical formula | C$_{33}$ H$_{42}$ Fe N$_6$ O$_{10.50}$ |
| Formula weight | 746.58 |
| Temperature | 150(1) K |
| Wavelength | 0.71073 Å |
| Crystal system | Triclinic |
| Space group | P-1 |
| Unit cell dimensions | a = 10.9760(4) Å  α = 94.283(2)°. |
| | b = 11.3790(4) Å  β = 90.351(2)°. |
| | c = 13.9952(5) Å  γ = 91.731(2)°. |
| Volume | 1742.18(11) Å$^3$ |
| Z | 2 |
| Density (calculated) | 1.423 Mg/m$^3$ |
| Absorption coefficient | 0.500 mm$^{-1}$ |
| F(000) | 784 |
| Crystal size | 0.30 × 0.14 × 0.04 mm$^3$ |
| Theta range for data collection | 2.62 to 25.00°. |
| Index ranges | −13 <= h <= 13, −13 <= k <= 13, −16 <= l <= 16 |
| Reflections collected | 16641 |
| Independent reflections | 6114 [R(int) = 0.0753] |
| Completeness to theta = 25.00° | 99.8% |
| Absorption correction | Semi-empirical from equivalents |
| Max. and min. transmission | 0.966 and 0.892 |
| Refinement method | Full-matrix least-squares on F$^2$ |
| Data/restraints/parameters | 6114/2/462 |

TABLE 5-continued

Crystal data and structure refinement for Fe(Apo6617)₃

| | |
|---|---|
| Goodness-of-fit on F² | 1.034 |
| Final R indices [I > 2sigma(I)] | R1 = 0.0566, wR2 = 0.1410 |
| R indices (all data) | R1 = 0.0830, wR2 = 0.1594 |
| Extinction coefficient | none |
| Largest diff. peak and hole | 0.609 and −0.539 e · Å⁻³ |

TABLE 6

Bond lengths [Å] and angles [°] for Fe(Apo6617)₃

| | |
|---|---|
| Fe(1)—O(5) | 1.985(2) |
| Fe(1)—O(8) | 2.010(2) |
| Fe(1)—O(2) | 2.016(2) |
| Fe(1)—O(7) | 2.020(3) |
| Fe(1)—O(4) | 2.025(2) |
| Fe(1)—O(1) | 2.048(2) |
| O(1)—C(1) | 1.294(4) |
| O(2)—C(5) | 1.327(4) |
| O(4)—C(12) | 1.299(4) |
| O(5)—C(17) | 1.321(4) |
| O(6)—C(20) | 1.233(4) |
| O(7)—C(24) | 1.297(4) |
| O(8)—C(28) | 1.329(4) |
| O(9)—C(31) | 1.218(4) |
| N(1)—C(3) | 1.351(5) |
| N(1)—C(4) | 1.397(5) |
| N(1)—C(7) | 1.487(5) |
| N(3)—C(14) | 1.355(5) |
| N(3)—C(16) | 1.390(5) |
| N(3)—C(19) | 1.483(5) |
| N(5)—C(26) | 1.361(5) |
| N(5)—C(27) | 1.387(4) |
| N(5)—C(30) | 1.474(5) |
| C(1)—C(2) | 1.393(5) |
| C(1)—C(5) | 1.434(5) |
| C(2)—C(3) | 1.383(6) |
| C(3)—C(6) | 1.495(5) |
| C(4)—C(5) | 1.384(5) |
| C(4)—C(8) | 1.493(6) |
| C(8)—O(3*) | 1.256(7) |
| C(8)—O(3) | 1.281(8) |
| C(8)—N(2*) | 1.325(8) |
| C(8)—N(2) | 1.378(8) |
| N(2)—C(9) | 1.608(12) |
| C(9)—C(10) | 1.447(16) |
| C(9)—C(11) | 1.505(16) |
| C(10)—C(11) | 1.581(16) |
| N(2*)—C(9*) | 1.556(13) |
| C(9*)—C(11*) | 1.440(12) |
| C(9*)—C(10*) | 1.454(15) |
| C(10*)—C(11*) | 1.474(14) |
| C(12)—C(13) | 1.384(5) |
| C(12)—C(17) | 1.441(5) |
| C(13)—C(14) | 1.393(5) |
| C(14)—C(18) | 1.498(5) |
| C(16)—C(17) | 1.383(5) |
| C(16)—C(20) | 1.508(5) |
| C(20)—N(4) | 1.331(5) |
| N(4)—C(21) | 1.474(10) |
| C(21)—C(23) | 1.434(15) |
| C(21)—C(22) | 1.492(13) |
| C(22)—C(23) | 1.392(15) |
| C(21*)—C(22*) | 1.461(19) |
| C(21*)—C(23*) | 1.535(16) |
| C(22*)—C(23*) | 1.582(18) |
| C(24)—C(25) | 1.395(5) |
| C(24)—C(28) | 1.425(5) |
| C(25)—C(26) | 1.363(5) |
| C(26)—C(29) | 1.504(5) |
| C(27)—C(28) | 1.376(5) |
| C(27)—C(31) | 1.501(5) |
| C(31)—N(6) | 1.310(5) |
| N(6)—C(32) | 1.514(12) |
| C(32)—C(34) | 1.417(15) |
| C(32)—C(33) | 1.485(16) |
| C(33)—C(34) | 1.459(15) |
| C(32*)—C(33*) | 1.433(16) |
| C(32*)—C(34*) | 1.53(2) |
| C(33*)—C(34*) | 1.45(2) |
| O(11)—O(11)#1 | 1.550(16) |
| O(5)—Fe(1)—O(8) | 88.36(9) |
| O(5)—Fe(1)—O(2) | 88.97(10) |
| O(8)—Fe(1)—O(2) | 95.35(10) |
| O(5)—Fe(1)—O(7) | 166.27(10) |
| O(8)—Fe(1)—O(7) | 80.41(10) |
| O(2)—Fe(1)—O(7) | 99.86(11) |
| O(5)—Fe(1)—O(4) | 81.11(10) |
| O(8)—Fe(1)—O(4) | 101.01(10) |
| O(2)—Fe(1)—O(4) | 160.54(10) |
| O(7)—Fe(1)—O(4) | 93.23(10) |
| O(5)—Fe(1)—O(1) | 103.01(10) |
| O(8)—Fe(1)—O(1) | 167.38(10) |
| O(2)—Fe(1)—O(1) | 79.61(10) |
| O(7)—Fe(1)—O(1) | 89.01(10) |
| O(4)—Fe(1)—O(1) | 86.34(10) |
| C(1)—O(1)—Fe(1) | 113.1(2) |
| C(5)—O(2)—Fe(1) | 114.4(2) |
| C(12)—O(4)—Fe(1) | 112.7(2) |
| C(17)—O(5)—Fe(1) | 113.2(2) |
| C(24)—O(7)—Fe(1) | 113.6(2) |
| C(28)—O(8)—Fe(1) | 112.7(2) |
| C(3)—N(1)—C(4) | 121.3(3) |
| C(3)—N(1)—C(7) | 117.7(3) |
| C(4)—N(1)—C(7) | 120.8(3) |
| C(14)—N(3)—C(16) | 121.3(3) |
| C(14)—N(3)—C(19) | 118.6(3) |
| C(16)—N(3)—C(19) | 120.1(3) |
| C(26)—N(5)—C(27) | 120.5(3) |
| C(26)—N(5)—C(30) | 120.7(3) |
| C(27)—N(5)—C(30) | 118.7(3) |
| O(1)—C(1)—C(2) | 124.9(4) |
| O(1)—C(1)—C(5) | 117.8(3) |
| C(2)—C(1)—C(5) | 117.3(3) |
| C(3)—C(2)—C(1) | 121.3(4) |
| N(1)—C(3)—C(2) | 120.4(3) |
| N(1)—C(3)—C(6) | 119.4(4) |
| C(2)—C(3)—C(6) | 120.2(4) |
| C(5)—C(4)—N(1) | 119.0(3) |
| C(5)—C(4)—C(8) | 121.6(3) |
| N(1)—C(4)—C(8) | 119.3(3) |
| O(2)—C(5)—C(4) | 124.3(3) |
| O(2)—C(5)—C(1) | 115.1(3) |
| C(4)—C(5)—C(1) | 120.6(3) |
| O(3*)—C(8)—O(3) | 26.2(4) |
| O(3*)—C(8)—N(2*) | 118.8(5) |
| O(3)—C(8)—N(2*) | 117.9(6) |
| O(3*)—C(8)—N(2) | 117.3(6) |
| O(3)—C(8)—N(2) | 127.8(6) |
| N(2*)—C(8)—N(2) | 22.3(4) |
| O(3*)—C(8)—C(4) | 125.0(4) |
| O(3)—C(8)—C(4) | 119.1(5) |
| N(2*)—C(8)—C(4) | 116.2(4) |
| N(2)—C(8)—C(4) | 112.9(4) |
| C(8)—N(2)—C(9) | 106.3(6) |
| C(10)—C(9)—C(11) | 64.7(7) |
| C(10)—C(9)—N(2) | 103.8(9) |
| C(11)—C(9)—N(2) | 113.2(8) |
| C(9)—C(10)—C(11) | 59.4(7) |
| C(9)—C(11)—C(10) | 55.8(7) |
| C(8)—N(2*)—C(9*) | 119.2(7) |
| C(11*)—C(9*)—C(10*) | 61.2(7) |
| C(11*)—C(9*)—N(2*) | 114.6(8) |
| C(10*)—C(9*)—N(2*) | 100.4(9) |
| C(9*)—C(10*)—C(11*) | 58.9(7) |
| C(9*)—C(11*)—C(10*) | 59.8(7) |
| O(4)—C(12)—C(13) | 125.6(3) |
| O(4)—C(12)—C(17) | 116.3(3) |
| C(13)—C(12)—C(17) | 118.0(3) |
| C(12)—C(13)—C(14) | 120.9(3) |
| N(3)—C(14)—C(13) | 120.2(3) |
| N(3)—C(14)—C(18) | 119.4(3) |
| C(13)—C(14)—C(18) | 120.5(4) |
| C(17)—C(16)—N(3) | 119.7(3) |

TABLE 6-continued

Bond lengths [Å] and angles [°] for Fe(Apo6617)₃

| | |
|---|---|
| C(17)—C(16)—C(20) | 120.0(3) |
| N(3)—C(16)—C(20) | 120.3(3) |
| O(5)—C(17)—C(16) | 123.9(3) |
| O(5)—C(17)—C(12) | 116.5(3) |
| C(16)—C(17)—C(12) | 119.7(3) |
| O(6)—C(20)—N(4) | 124.1(4) |
| O(6)—C(20)—C(16) | 122.9(3) |
| N(4)—C(20)—C(16) | 113.0(3) |
| C(20)—N(4)—C(21) | 126.2(5) |
| C(23)—C(21)—N(4) | 120.5(8) |
| C(23)—C(21)—C(22) | 56.8(7) |
| N(4)—C(21)—C(22) | 118.0(7) |
| C(23)—C(22)—C(21) | 59.5(7) |
| C(22)—C(23)—C(21) | 63.7(8) |
| C(22*)—C(21*)—C(23*) | 63.7(8) |
| C(21*)—C(22*)—C(23*) | 60.4(8) |
| C(21*)—C(23*)—C(22*) | 55.9(8) |
| O(7)—C(24)—C(25) | 125.8(3) |
| O(7)—C(24)—C(28) | 116.6(3) |
| C(25)—C(24)—C(28) | 117.5(3) |
| C(26)—C(25)—C(24) | 121.9(4) |
| N(5)—C(26)—C(25) | 120.1(3) |
| N(5)—C(26)—C(29) | 118.4(3) |
| C(25)—C(26)—C(29) | 121.5(4) |
| C(28)—C(27)—N(5) | 120.4(3) |
| C(28)—C(27)—C(31) | 120.9(3) |
| N(5)—C(27)—C(31) | 118.6(3) |
| O(8)—C(28)—C(27) | 123.8(3) |
| O(8)—C(28)—C(24) | 116.6(3) |
| C(27)—C(28)—C(24) | 119.5(3) |
| O(9)—C(31)—N(6) | 123.8(4) |
| O(9)—C(31)—C(27) | 121.5(3) |
| N(6)—C(31)—C(27) | 114.7(3) |
| C(31)—N(6)—C(32) | 119.2(5) |
| C(34)—C(32)—C(33) | 60.3(8) |
| C(34)—C(32)—N(6) | 126.8(9) |
| C(33)—C(32)—N(6) | 118.8(8) |
| C(34)—C(33)—C(32) | 57.5(7) |
| C(32)—C(34)—C(33) | 62.2(7) |
| C(33*)—C(32*)—C(34*) | 58.7(9) |
| C(32*)—C(33*)—C(34*) | 64.0(9) |
| C(33*)—C(34*)—C(32*) | 57.3(8) |

TABLE 7

Crystal data and structure refinement for Fe(Apo6619)₃

| | |
|---|---|
| Identification code | Fe(Apo6619)₃ |
| Empirical formula | C37.50 H53.50 Fe N7.50 O12.50 |
| Formula weight | 865.23 |
| Temperature | 150(1) K |
| Wavelength | 0.71073 Å |
| Crystal system | Triclinic |
| Space group | P-1 |
| Unit cell dimensions | a = 11.9319(8) Å  α = 116.811(3)°. |
| | b = 14.3968(9) Å  β = 108.353(3)°. |
| | c = 15.3024(9) Å  γ = 95.164(4)°. |
| Volume | 2141.6(2) Å³ |
| Z | 2 |
| Density (calculated) | 1.342 Mg/m³ |
| Absorption coefficient | 0.421 mm⁻¹ |
| F(000) | 914 |
| Crystal size | 0.22 × 0.21 × 0.10 mm³ |
| Theta range for data collection | 2.62 to 27.59°. |
| Index ranges | −15 <= h <= 14, −18 <= k <= 18, −16 <= l <= 19 |
| Reflections collected | 20782 |
| Independent reflections | 9756 [R(int) = 0.0469] |
| Completeness to theta = 27.59° | 98.4% |
| Absorption correction | Semi-empirical from equivalents |
| Max. and min. transmission | 0.949 and 0.805 |
| Refinement method | Full-matrix least-squares on F² |
| Data/restraints/parameters | 9756/0/518 |
| Goodness-of-fit on F² | 1.053 |
| Final R indices [I > 2sigma(I)] | R1 = 0.0582, wR2 = 0.1519 |

TABLE 7-continued

Crystal data and structure refinement for Fe(Apo6619)₃

| | |
|---|---|
| R indices (all data) | R1 = 0.0928, wR2 = 0.1663 |
| Extinction coefficient | 0.0061(14) |
| Largest diff. peak and hole | 0.559 and −0.504 e · Å⁻³ |

TABLE 8

Bond lengths [Å] and angles [°] for Fe(Apo6619)₃

| | |
|---|---|
| Fe(1)—O(5) | 1.9725(19) |
| Fe(1)—O(3) | 2.0180(17) |
| Fe(1)—O(4) | 2.0185(19) |
| Fe(1)—O(6) | 2.0300(18) |
| Fe(1)—O(2) | 2.0320(18) |
| Fe(1)—O(1) | 2.0634(17) |
| O(1)—C(1) | 1.312(3) |
| O(2)—C(2) | 1.292(3) |
| O(3)—C(12) | 1.314(3) |
| O(4)—C(13) | 1.294(3) |
| O(5)—C(23) | 1.323(3) |
| O(6)—C(24) | 1.295(3) |
| O(7)—C(10) | 1.250(3) |
| O(8)—C(21) | 1.244(3) |
| O(9)—C(32) | 1.249(3) |
| N(1)—C(4) | 1.362(4) |
| N(1)—C(5) | 1.410(3) |
| N(1)—C(7) | 1.466(4) |
| N(2)—C(15) | 1.359(4) |
| N(2)—C(16) | 1.393(3) |
| N(2)—C(18) | 1.465(3) |
| N(3)—C(26) | 1.373(4) |
| N(3)—C(27) | 1.382(3) |
| N(3)—C(29) | 1.469(4) |
| N(4)—C(10) | 1.329(4) |
| N(4)—C(11) | 1.464(4) |
| N(5)—C(21) | 1.319(4) |
| N(5)—C(22) | 1.449(4) |
| N(6)—C(32) | 1.317(4) |
| N(6)—C(33) | 1.466(4) |
| C(1)—C(5) | 1.394(4) |
| C(1)—C(2) | 1.442(4) |
| C(2)—C(3) | 1.392(4) |
| C(3)—C(4) | 1.383(4) |
| C(4)—C(6) | 1.498(4) |
| C(5)—C(10) | 1.485(4) |
| C(7)—C(8) | 1.480(5) |
| C(7)—C(9) | 1.481(5) |
| C(8)—C(9) | 1.500(6) |
| C(12)—C(16) | 1.370(4) |
| C(12)—C(13) | 1.438(4) |
| C(13)—C(14) | 1.393(4) |
| C(14)—C(15) | 1.387(4) |
| C(15)—C(17) | 1.494(4) |
| C(16)—C(21) | 1.512(4) |
| C(18)—C(19) | 1.486(4) |
| C(18)—C(20) | 1.493(4) |
| C(19)—C(20) | 1.488(5) |
| C(23)—C(27) | 1.377(4) |
| C(23)—C(24) | 1.438(4) |
| C(24)—C(25) | 1.398(4) |
| C(25)—C(26) | 1.372(4) |
| C(26)—C(28) | 1.500(4) |
| C(27)—C(32) | 1.494(4) |
| C(29)—C(31) | 1.480(5) |
| C(29)—C(30) | 1.481(4) |
| C(30)—C(31) | 1.494(5) |
| N(1S)—C(2S) | 1.345(6) |
| N(1S)—C(1S) | 1.367(7) |
| N(1S)—C(3S) | 1.442(5) |
| O(1S)—C(2S) | 1.253(6) |
| O(5)—Fe(1)—O(3) | 90.66(7) |
| O(5)—Fe(1)—O(4) | 161.25(7) |
| O(3)—Fe(1)—O(4) | 80.33(7) |
| O(5)—Fe(1)—O(6) | 80.93(7) |
| O(3)—Fe(1)—O(6) | 106.44(7) |
| O(4)—Fe(1)—O(6) | 85.88(7) |

TABLE 8-continued

| Bond lengths [Å] and angles [°] for Fe(Apo6619)₃ | |
|---|---|
| O(5)—Fe(1)—O(2) | 93.91(8) |
| O(3)—Fe(1)—O(2) | 85.84(7) |
| O(4)—Fe(1)—O(2) | 101.72(8) |
| O(6)—Fe(1)—O(2) | 166.63(7) |
| O(5)—Fe(1)—O(1) | 103.56(7) |
| O(3)—Fe(1)—O(1) | 159.41(7) |
| O(4)—Fe(1)—O(1) | 89.78(7) |
| O(6)—Fe(1)—O(1) | 90.66(7) |
| O(2)—Fe(1)—O(1) | 78.50(7) |
| C(1)—O(1)—Fe(1) | 113.92(16) |
| C(2)—O(2)—Fe(1) | 115.03(16) |
| C(12)—O(3)—Fe(1) | 112.01(16) |
| C(13)—O(4)—Fe(1) | 112.70(16) |
| C(23)—O(5)—Fe(1) | 113.72(16) |
| C(24)—O(6)—Fe(1) | 112.55(16) |
| C(4)—N(1)—C(5) | 121.5(2) |
| C(4)—N(1)—C(7) | 118.7(2) |
| C(5)—N(1)—C(7) | 119.7(2) |
| C(15)—N(2)—C(16) | 121.5(2) |
| C(15)—N(2)—C(18) | 120.4(2) |
| C(16)—N(2)—C(18) | 118.1(2) |
| C(26)—N(3)—C(27) | 121.0(2) |
| C(26)—N(3)—C(29) | 119.8(2) |
| C(27)—N(3)—C(29) | 119.2(2) |
| C(10)—N(4)—C(11) | 121.8(2) |
| C(21)—N(5)—C(22) | 121.9(2) |
| C(32)—N(6)—C(33) | 120.9(3) |
| O(1)—C(1)—C(5) | 124.9(2) |
| O(1)—C(1)—C(2) | 115.5(2) |
| C(5)—C(1)—C(2) | 119.3(2) |
| O(2)—C(2)—C(3) | 124.8(3) |
| O(2)—C(2)—C(1) | 116.8(2) |
| C(3)—C(2)—C(1) | 118.4(2) |
| C(4)—C(3)—C(2) | 121.1(3) |
| N(1)—C(4)—C(3) | 120.0(2) |
| N(1)—C(4)—C(6) | 119.6(2) |
| C(3)—C(4)—C(6) | 120.3(3) |
| C(1)—C(5)—N(1) | 118.5(2) |
| C(1)—C(5)—C(10) | 122.0(2) |
| N(1)—C(5)—C(10) | 118.7(2) |
| N(1)—C(7)—C(8) | 118.2(3) |
| N(1)—C(7)—C(9) | 119.6(3) |
| C(8)—C(7)—C(9) | 60.9(3) |
| C(7)—C(8)—C(9) | 59.6(3) |
| C(7)—C(9)—C(8) | 59.5(2) |
| O(7)—C(10)—N(4) | 121.7(3) |
| O(7)—C(10)—C(5) | 123.0(3) |
| N(4)—C(10)—C(5) | 115.2(2) |
| O(3)—C(12)—C(16) | 125.1(3) |
| O(3)—C(12)—C(13) | 116.0(2) |
| C(16)—C(12)—C(13) | 118.8(2) |
| O(4)—C(13)—C(14) | 124.3(2) |
| O(4)—C(13)—C(12) | 116.9(2) |
| C(14)—C(13)—C(12) | 118.8(2) |
| C(15)—C(14)—C(13) | 120.7(3) |
| N(2)—C(15)—C(14) | 119.4(2) |
| N(2)—C(15)—C(17) | 120.4(2) |
| C(14)—C(15)—C(17) | 120.1(3) |
| C(12)—C(16)—N(2) | 120.3(2) |
| C(12)—C(16)—C(21) | 121.5(2) |
| N(2)—C(16)—C(21) | 117.8(2) |
| N(2)—C(18)—C(19) | 118.1(2) |
| N(2)—C(18)—C(20) | 119.1(2) |
| C(19)—C(18)—C(20) | 59.9(2) |
| C(18)—C(19)—C(20) | 60.3(2) |
| C(19)—C(20)—C(18) | 59.8(2) |
| O(8)—C(21)—N(5) | 124.0(3) |
| O(8)—C(21)—C(16) | 119.9(2) |
| N(5)—C(21)—C(16) | 116.1(2) |
| O(5)—C(23)—C(27) | 124.7(2) |
| O(5)—C(23)—C(24) | 115.9(2) |
| C(27)—C(23)—C(24) | 119.3(2) |
| O(6)—C(24)—C(25) | 125.3(2) |
| O(6)—C(24)—C(23) | 116.7(2) |

TABLE 8-continued

| Bond lengths [Å] and angles [°] for Fe(Apo6619)₃ | |
|---|---|
| C(25)—C(24)—C(23) | 118.0(2) |
| C(26)—C(25)—C(24) | 121.4(3) |
| C(25)—C(26)—N(3) | 119.8(2) |
| C(25)—C(26)—C(28) | 120.6(3) |
| N(3)—C(26)—C(28) | 119.6(2) |
| C(23)—C(27)—N(3) | 120.5(2) |
| C(23)—C(27)—C(32) | 120.8(2) |
| N(3)—C(27)—C(32) | 118.3(2) |
| N(3)—C(29)—C(31) | 119.3(3) |
| N(3)—C(29)—C(30) | 118.4(3) |
| C(31)—C(29)—C(30) | 60.6(2) |
| C(29)—C(30)—C(31) | 59.7(2) |
| C(29)—C(31)—C(30) | 59.7(2) |
| O(9)—C(32)—N(6) | 123.8(3) |
| O(9)—C(32)—C(27) | 120.8(2) |
| N(6)—C(32)—C(27) | 115.4(3) |
| C(2S)—N(1S)—C(1S) | 119.6(5) |
| C(2S)—N(1S)—C(3S) | 117.8(4) |
| C(1S)—N(1S)—C(3S) | 122.5(5) |
| O(1S)—C(2S)—N(1S) | 120.9(6) |

The invention claimed is:

1. A 3-hydroxypyridin-4-one compound of formula I:

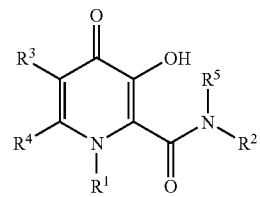

wherein: $R^1$ is X with the proviso that $R^2R^5N$ are taken together to form a heterocyclic ring selected from the group consisting of piperidinyl, morpholinyl, pyrrolidinyl and piperazinyl, wherein the piperidinyl, morpholinyl, pyrrolidinyl or piperazinyl group is either unsubstituted or substituted with one to three $C_1$ to $C_6$ alkyl groups; X is $C_3$-$C_6$ cycloalkyl; $R^3$ is selected from the group consisting of hydrogen and $C_1$ to $C_6$ alkyl; and $R^4$ is selected from the group consisting of hydrogen and $C_1$ to $C_6$ alkyl; or a pharmaceutically acceptable salt thereof.

2. A compound of claim 1 wherein X is cyclopropyl, $R^3$ is hydrogen, $R^4$ is methyl and the heterocyclic ring is unsubstituted morpholinyl and wherein said compound is 1-cyclopropyl-3-hydroxy-6-methyl-2-(morpholin-4-ylcarbonyl)pyridine-3(1H)-one.

3. A compound of claim 2 wherein X is cyclopropyl, $R^3$ is hydrogen, $R^4$ is methyl and the heterocyclic ring is piperizinyl substituted with one to three $C_1$ to $C_6$ alkyl groups.

4. A compound of claim 3 wherein the piperizinyl is substituted with a methyl group and wherein said compound is 1-cyclopropyl-3-hydroxy-6-methyl-2-[(4-methylpiperazin-1-yl)carbonyl]pyridine-4-(1H)-one.

5. A pharmaceutical composition comprising a compound according to any one of claims 1 to 4 and a pharmaceutically acceptable carrier.

6. The pharmaceutical composition of claim 5, which is adopted for oral administration.

* * * * *